(12) United States Patent
Yuyama et al.

(10) Patent No.: US 8,733,217 B2
(45) Date of Patent: May 27, 2014

(54) DEVICE AND METHOD FOR DISPENSING MEDICINE

(75) Inventors: Shoji Yuyama, Osaka (JP); Takayuki Fujikawa, Osaka (JP); Naoki Koike, Osaka (JP)

(73) Assignee: Yuyama Mfg. Co., Ltd., Osaka (JP)

( * ) Notice: Subject to any disclaimer, the term of this patent is extended or adjusted under 35 U.S.C. 154(b) by 543 days.

(21) Appl. No.: 13/119,906

(22) PCT Filed: Sep. 18, 2009

(86) PCT No.: PCT/JP2009/004714
§ 371 (c)(1),
(2), (4) Date: Mar. 18, 2011

(87) PCT Pub. No.: WO2010/032479
PCT Pub. Date: Mar. 25, 2010

(65) Prior Publication Data
US 2011/0168733 A1  Jul. 14, 2011

(30) Foreign Application Priority Data

Sep. 19, 2008 (JP) ................. 2008-241652
Mar. 24, 2009 (JP) ................. 2009-072877
Jul. 23, 2009 (JP) ................. 2009-172207
Sep. 16, 2009 (JP) ................. 2009-214317

(51) Int. Cl.
*B65D 83/00* (2006.01)
*B65D 83/04* (2006.01)
*A61J 1/00* (2006.01)

(52) U.S. Cl.
USPC .................... 83/13; 221/1; 221/31

(58) Field of Classification Search
USPC ......... 83/13, 14, 72, 78, 42, 39, 56, 256, 614, 83/948, 35, 74, 368, 371, 404.1, 419; 221/151, 277, 1, 30, 31; 53/484
See application file for complete search history.

(56) References Cited

U.S. PATENT DOCUMENTS

| 4,546,901 A * | 10/1985 | Buttarazzi ................. 221/10 |
| 7,316,328 B2 | 1/2008 | Yuyama et al. |
| 7,822,505 B2 | 10/2010 | Yuyama et al. |
| 8,083,078 B2 | 12/2011 | Omura et al. |
| 2003/0131702 A1* | 7/2003 | Sauer et al. ................. 83/23 |
| 2008/0236352 A1* | 10/2008 | Kim ................. 83/84 |

FOREIGN PATENT DOCUMENTS

| JP | 4-272758 | 9/1992 |
| JP | 2818759 | 8/1998 |
| JP | 3083165 | 6/2000 |
| JP | 2006-109854 | 4/2006 |
| JP | 2006-109858 | 4/2006 |

(Continued)

*Primary Examiner* — Ghassem Alie
(74) *Attorney, Agent, or Firm* — Jones Day

(57) ABSTRACT

A medicine dispensing device may include: a device body; a container containing a plurality of blister packs with medicines packaged individually as arranged one behind another and being attached to the device body such that the blister packs are horizontally arranged one behind another; a dispensing member movably provided in the device body and being moved up to the container to dispense the blister pack contained in the container; a gripping member gripping and carrying the blister pack dispensed by the dispensing member; and a cutting member cutting off a fraction from the blister pack gripped and carried by the gripping member. Depending upon the opened positions of an opening/closing door, one sheet of the blister pack is dispensed as it is or the fraction thereof is dispensed.

8 Claims, 26 Drawing Sheets

(56) References Cited

FOREIGN PATENT DOCUMENTS

| JP | 2006-109859 | 4/2006 |
| JP | 2006-158552 | 6/2006 |
| TW | 200702257 A | 1/2007 |
| TW | I295573 | 4/2008 |

* cited by examiner

FIG. 9
(a)
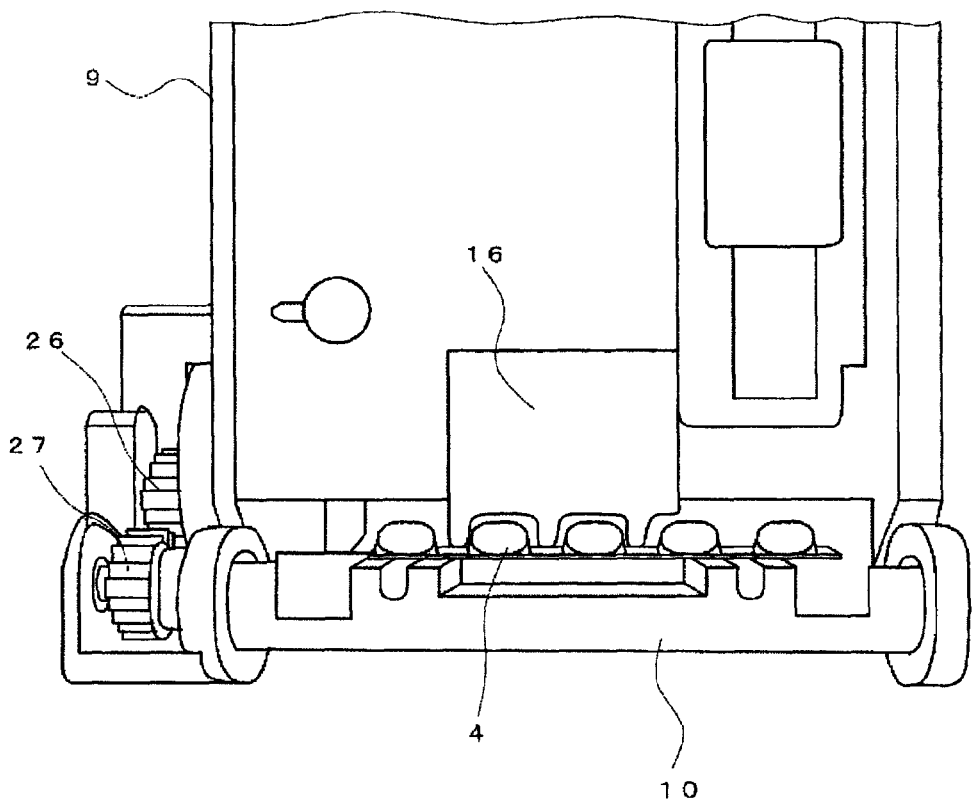
(b)
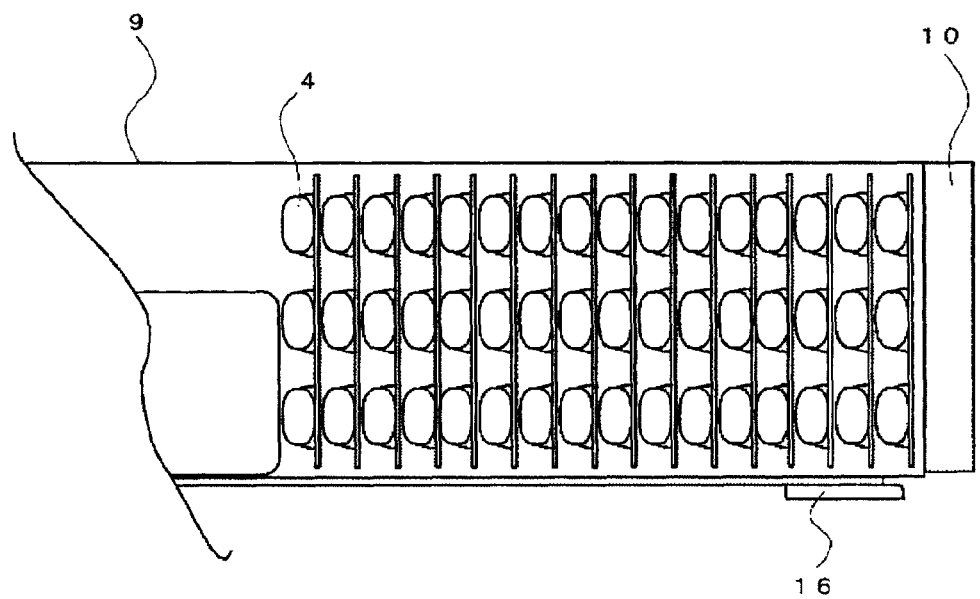

DEVICE AND METHOD FOR DISPENSING MEDICINE

CROSS-REFERENCE TO RELATED APPLICATIONS

This application is a national stage filing under 35 U.S.C. §371 of International Patent Application No. PCT/JP2009/004714, filed Sep. 18, 2009, the entire contents of which are incorporated herein by reference, which claims the benefit of the following applications, the entire contents of each of which are incorporated herein by reference:

Japanese Patent Application No. 2008-241652, filed Sep. 19, 2008;

Japanese Patent Application No. 2009-072877, filed Mar. 24, 2009;

Japanese Patent Application No. 2009-172207, filed Jul. 23, 2009; and

Japanese Patent Application No. 2009-214317, filed Sep. 16, 2009.

TECHNICAL FIELD

The present invention relates to a device and method for dispensing medicine.

BACKGROUND OF THE INVENTION

There exists a medicine dispensing device for dispensing blister packs configured to grip a blister pack by a grip unit and dispense a necessary quantity of sheet packages after cutting the blister pack by a cutter mechanism (see, e.g., Patent Document 1).

Further, there exists another medicine dispensing device for dispensing blister packs configured to perform suction and dispense a blister pack contained in a medicine cassette by a suctioning member (see, e.g., Patent Document 2).

However, the medicine dispensing device disclosed in Patent Document 1 is problematic in that the grip unit is used not only for dispensing the fraction of the blister pack, but also for dispensing one sheet of the blister pack as it is, thus deteriorating dispensing efficiency. It is further problematic in that the vertical stack of the blister packs increases occupancy space in a height direction and restricts the quantity and type of the blister packs to be contained.

Further, the medicine dispensing device disclosed in Patent Document 2 cannot dispense the fraction of the blister pack.

Patent Document 1: Japanese Patent No. 2818759
Patent Document 2: Japanese Laid-Open Patent Application No. 2006-109859

SUMMARY OF THE INVENTION

Thus, it is an object of the present invention to provide a medicine dispensing device configured to accommodate a large quantity of blister packs and appropriately dispense a fraction of the blister pack while achieving rapid dispensing operation. It is another object of the present invention to provide a method of dispensing medicine As measures for achieving the foregoing object, the present invention provides a medicine dispensing device including the following: a device body; a container containing a plurality of blister packs with medicines packaged individually therein as the blister packs are arranged one behind another, the container being attached to the device body such that the blister packs are horizontally or substantially horizontally arranged one behind another; a dispensing member movably provided in the device body and moved up to the container to dispense the contained blister pack; a gripping member gripping and carrying the blister pack dispensed by the dispensing member; and a cutting member cutting off a fraction from the blister pack gripped and carried by the gripping member. The container includes: a dispensing opening formed in a bottom of the container at one end of the container for dispensing the blister pack; a biasing means for biasing the contained blister packs toward the one end; and an opening/closing door disposed at one end surface. The opening/closing door includes a retaining portion retaining the blister pack ejected from the dispensing opening of the container. The opening/closing door is positionable to a closed position for prohibiting the dispensing member from dispensing the blister pack, a first opened position for permitting the dispensing member to dispense the blister pack and a second opened position for permitting the dispensing member to dispense the blister pack and retaining the dispensed blister pack to the retaining portion. The gripping member is configured to grip the blister pack retained by the retaining portion in the second opened position and to carry the blister pack to the cutting member, the gripping member being further configured to carry the remainder of the blister pack with the fraction cut off for retention in the retaining portion.

According to such construction, when dispensing one sheet of the blister pack as it is, the opening/closing door is positioned to the first opened position and the blister pack can be pushed down and dispensed through the dispensing opening by the dispensing member. Accordingly, dispensing operation can be rapidly performed. Further, when dispensing the fraction of the blister pack, the opening/closing door is positioned to the second opened position and the blister pack ejected from the dispensing opening is retained by the holding portion. Subsequently, the blister pack is carried to the cutting member by the gripping member and is then cut, thus dispensing the desired fraction.

Preferably, the medicine dispensing device further includes a position adjusting member adjusting a relative position between the blister pack gripped by the gripping member and the cutting member to change a cutting position for the blister pack.

Preferably, the dispensing member includes a push-down portion pushing down the blister pack located at the one end of the container. Further, the container preferably includes a communication portion permitting a movement of the push-down portion at the one end surface. Also, the opening/closing door prohibits the movement of the push-down portion in the communication portion in the closed position.

The dispensing opening of the container may be covered at least in part by a closure piece biased to the closed position by a spring.

When a closure piece fixed to the container closes the dispensing opening in part, the dispensing opening of the container may form a gap that permits one sheet of the blister pack located at the one end to pass therethrough.

Preferably, the closure piece includes a curved portion curved upwardly at a leading end projecting to the dispensing opening According to such construction, when the foremost blister pack reaches the curved portion of the closure piece, only the foremost blister pack is moved upwardly along the curved portion and is shifted with respect to the neighboring next blister pack. Thus, only the foremost blister pack can be reliably discharged from the dispensing opening.

Preferably, the container is configured to open the opening/closing door when the container is drawn out from the device body and is positioned to a medicine dispensing position.

According to such configuration, the containers can be arranged in the device body with high density (e.g., without any gap upwardly and downwardly leftward and rightward)

Preferably, the blister pack contains a plurality of medicines in two rows. Preferably, the medicine dispensing device further includes a control means, which allows the cutting means to first cut one of the rows in a range that a remainder number after cutting does not become one and further to cut the other of the rows when the blister pack is cut by the cutting member based on a fraction order included in a medicine dispensing instruction.

According to such construction, the blister pack can be cut by using a single cutting member so that the remainder number of medicines cannot become one. Further, it is possible to previously prevent the medicine from being taken by mistake as it is packaged.

Preferably, the control means allows the other of the rows to be cut first when the remainder number of the one of the rows is less than a remainder number of the other of the rows and the remainder number of the other of the rows is equal to or less than a fraction order number.

According to such configuration, each row of the blister pack can be cut with good balance.

Preferably, when a fraction order number indicated in the fraction order is greater than the remainder number of the one of the rows of the blister pack, the control means divides the fraction order number and allows the one of the rows to be cut by an obtained division number and thereafter allows the other of the rows to be cut.

According to such configuration, each row of the blister pack can be cut with good balance.

Preferably, a guide plate is disposed on the bottom of the container along a biased direction of the contained blister packs. The guide plate includes a first guide surface gradually higher toward the dispensing opening and a second guide surface connected to the first guide surface and being gradually lower toward the dispensing opening.

According to such construction, when the foremost blister pack passes over the first guide surface, it is shifted with respect to the immediately adjacent blister pack. Further, as for the curved foremost blister pack, when such a blister pack reaches the second guide surface, a force for straightening its shape is exerted to the blister pack. Accordingly, the blister pack can be dispensed smoothly each one sheet.

Preferably, the container includes a curvature receptor projecting inwardly from an inner end surface located at the dispensing opening. The curvature receptor includes a flat surface configured to abut a sheet surface of the blister pack and a curved surface forming a relief for a swelled portion of a curved blister pack.

According to such construction, even if the blister pack is curved, the swelled portion due to such curvature can be positioned to a concave portion forming the curved surface and the blister pack can be pushed down by the push-down portion.

Preferably, the push-down portion includes a first receptor configured to push down a side edge of a sheet portion of an even blister pack and a second receptor configured to abut and push down a sheet surface of a curved blister pack.

According to such construction, when the blister pack is even or is curved slightly, the first receptor can push down the blister pack. When the blister pack is considerably curved, the second receptor can push down the blister pack.

According to the present invention, different opened positions of the opening/closing door allow for not only dispensing the fraction, but also for rapidly dispensing one sheet of the blister pack as it is. Further, the container contains the blister packs such that the blister packs are horizontally or substantially horizontally arranged one behind another. This can reduce a vertical occupancy space when a plurality of the containers are mounted in the device body.

BRIEF DESCRIPTION OF THE DRAWINGS

FIG. 9(a) is a schematic fragmentary plan view showing a cassette in accordance with another embodiment and FIG. 9(b) is a side view thereof.

DESCRIPTION OF REFERENCE NUMERALS

Figure 1:
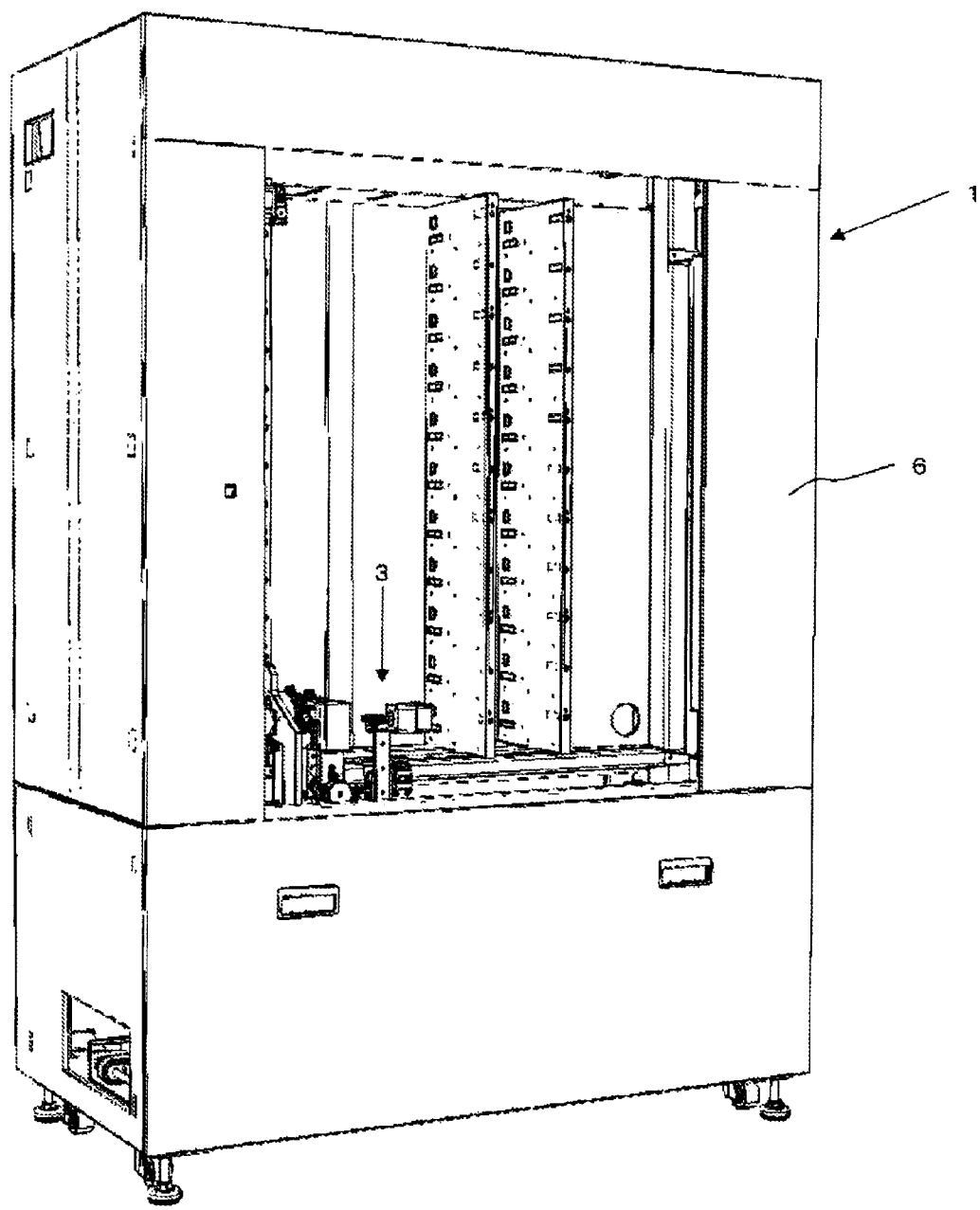
FIG. 1 is a perspective view showing an external configuration of a medicine dispensing device in accordance with one embodiment.

1 ... Device Body, 2 ... Cassette (Container), 3 ... Dispensing Member, 4 ... Blister pack, 5 ... Frame Body, 6 ... External panel, 7 ... Conveying Device, 8 ... Cassette mount, 9 ... Cassette Body, 10 ... Opening/closing Door, 11 ... Guide Groove, 12 ... Extruding Member, 13 ... Slide Portion, 14 ... Pusher piece, 15 ... Dispensing opening, 16 ... Closure Piece, 17 ... Spring, 18 ... Communication Portion, 19 ... Stepped Portion, 20 ... Engaging Piece, 21 ... Front Portion, 22 ... Guide Portion, 23 ... Cutout Portion, 24 ... Drive Mechanism, 25 ... Push bar, 26 ... First Gear, 27 ... Second Gear, 28 ... Engaging gear, 29 ... Manipulation Portion, 30 ... Magnetic Portion, 31 ... Light-emitting Portion, 32 ... Base, 33 ... First Dispensing Member, 34 ... Second Dispensing Member, 35 ... Gripping Member, 36 ... Cutting Member, 37 ... Collecting Member, 38 ... Vertical Rail, 39 ... Horizontal Rail, 40 ... Rack, 41 ... Push-down Portion, 42 ... Solenoid Portion, 43 ... Pusher, 44 ... Moving Piece, 45 ... Screw, 46 ... Front Plate, 47 ... Rear plate, 48 ... Supporter, 49 ... Fixed Blade, 50 ... Movable Blade, 51 ... Rotating Plate, 52 ... Guide Passage, 53 ... Collecting Container, 100 ... Cassette, 101 ... Cassette Body, 102 ... Opening/closing Door, 103 ... Constant force spring, 104 ... Through Aperture, 105 ... Guide Aperture, 106 ... Engaging aperture, 107 ... Door Body, 108 ... Opening/closing Member, 109 ... Pressure plate, 110 ... Threaded Hole, 111 ... Retaining recess, 112 ... Guide Recess, 113 ... Relief Groove, 114 ... Push-down piece, 115 ... Door Body Bearing Portion, 116 ... Protrusion Claw, 117 ... Opening/closing Supporting Portion, 118 ... Opening/closing Plate, 119 ... Aim Portion, 120 ... Spindle, 121 ... Manipulation Aperture, 122 ... First Flat Portion, 123 ... Second Flat Portion, 124 ... Depression, 125 ... Opening, 126 ... Cutout Portion, 127 ... Engaging Protrusion, 128 ... Pressure plate bearing portion, 133 ... First Dispensing Member, 134 ... Drive Mechanism, 135 ... Attach plate, 136 ... Motor, 137 ... Drive Gear, 138 ... Intermediate Gear, 139 ... Driven Gear, 140 ... Pivot pin, 141 ... Driven Plate, 142 ... Tray Feeding Unit, 143 ... Tray stacking unit, 144 ... Conveyance Line, 145 ... Journal Printer, 146 ... Indication Slip, 147 ... LED, 148 ... Tray, 149 ... Medicine Dispensing Device, 150 ... Filling unit, 151 ... Slope surface, 152 ... Display Panel, 153 ... Barcode Reader, 154 ... "MANUAL INPUT" Button, 155 ... "AUTOMATIC COUNT" Button, 156 ... Ten Key, 157 ... "TRANSMISSION" Button, 158 ... Length Measurement Sensor, 159 ... Spring, 200 ... Blister pack, 201 ... Gripping Section, 210 ... Cassette, 211 ... Cassette Body, 211a ... Protrusion Claw, 212 ... Opening/closing Door, 213 ... Extruding Member, 213a ... Hollow, 213b ... Flange, 213c ... Recess, 214 ... Guide Plate, 215 ... Communication Opening, 216 ... Pressure Piece, 300 ... Cassette, 301 ... Blister pack, 301a ... Sheet Portion, 301b ... Sheet Surface, 302 ... Cassette Body, 303 ... End Plate, 303a ... Attaching Groove, 304 ... Curvature receptor, 304a ... Curved Surface, 304b ... Flat Surface, 305 ... Attaching Portion, 306 ... Guide Plate, 307 ... First Curved Surface, 308 ... Second Curved Surface, 309 ... Dispensing opening, 310 ... Push-down Portion, 311 ... Guide Portion, 312 ... First Receptor, 312a ... First Receptor Surface, 312b ... Flat Surface, 313 ... Second Receptor, 313a ... Second Receptor Surface, 314 ... Frictional portion

DETAILED DESCRIPTION OF THE INVENTION

Embodiments of the present invention will be described with reference to the accompanying drawings. In the below description, the types, combinations, shapes, relative arrangement, etc. of elements or components are not intended to limit the scope of the present invention as described as such, unless specifically described. Further, where necessary, the terms (e.g., "upper," "lower," "front," "rear," "one end," "opposite end," etc.) are appropriately used herein for indicating a particular direction or position. However, those terms used herein are for easy understanding of the present invention with reference to the drawings and are not intended to limit the scope of the present invention on their meanings.

Configuration

Figure 2:
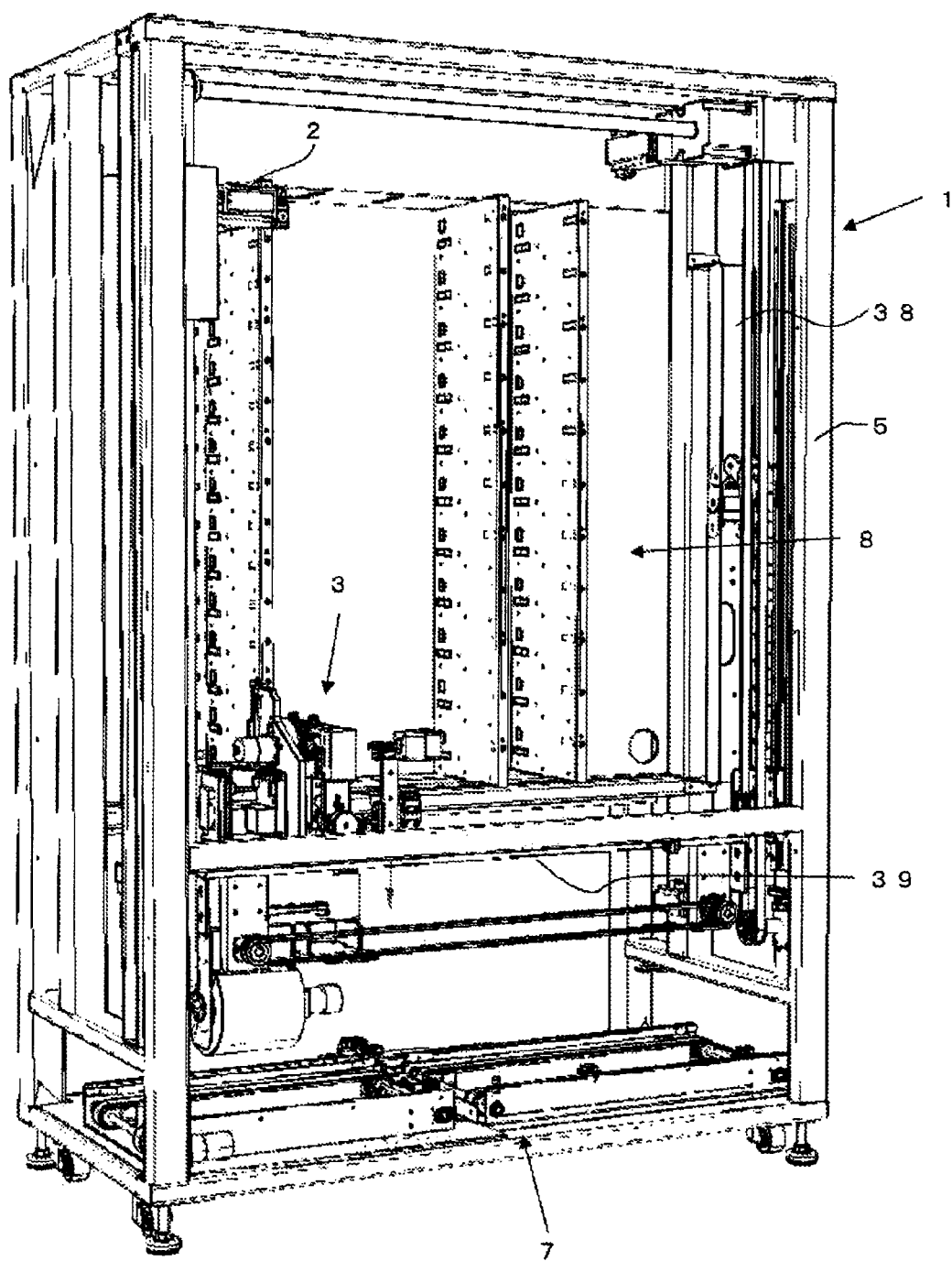
FIG. 2 is a perspective view showing when external panels are removed from FIG. 1.

FIGS. 1 and 2 schematically show a medicine dispensing device in accordance with one embodiment. The medicine dispensing device is constructed such that a plurality of cassettes 2 (container) are mounted in a device body 1 in a lattice arrangement without any clearance therebetween and a dispensing member 3 sequentially dispenses blister packs 4 with a plurality of medicines packaged therein from each of the cassettes 2. A series of operations of dispensing the blister packs 4 are performed by a control unit based on prescription data inputted from a host computer (not shown).

The device body 1 includes a frame body 5 and external panels 6 attached around the frame body, wherein the device body has a generally rectangular parallelepiped shape. A conveying unit 7 for conveying trays (not shown) is provided in a lower area of the device body. The device body has a cassette mount 8 in an upper area of its rear half. In this embodiment, the conveying unit 7 includes a roller conveyor. Other types of conveying means such as a belt conveyor, a pusher, etc. may be used as the conveying unit. The cassette mount 8 is constructed such that guide grooves (not shown) are formed on opposite surfaces of support panels arranged leftward and rightward at predetermined intervals and the cassettes 2 are inserted to and thus mounted on the guide grooves.

Figure 3:
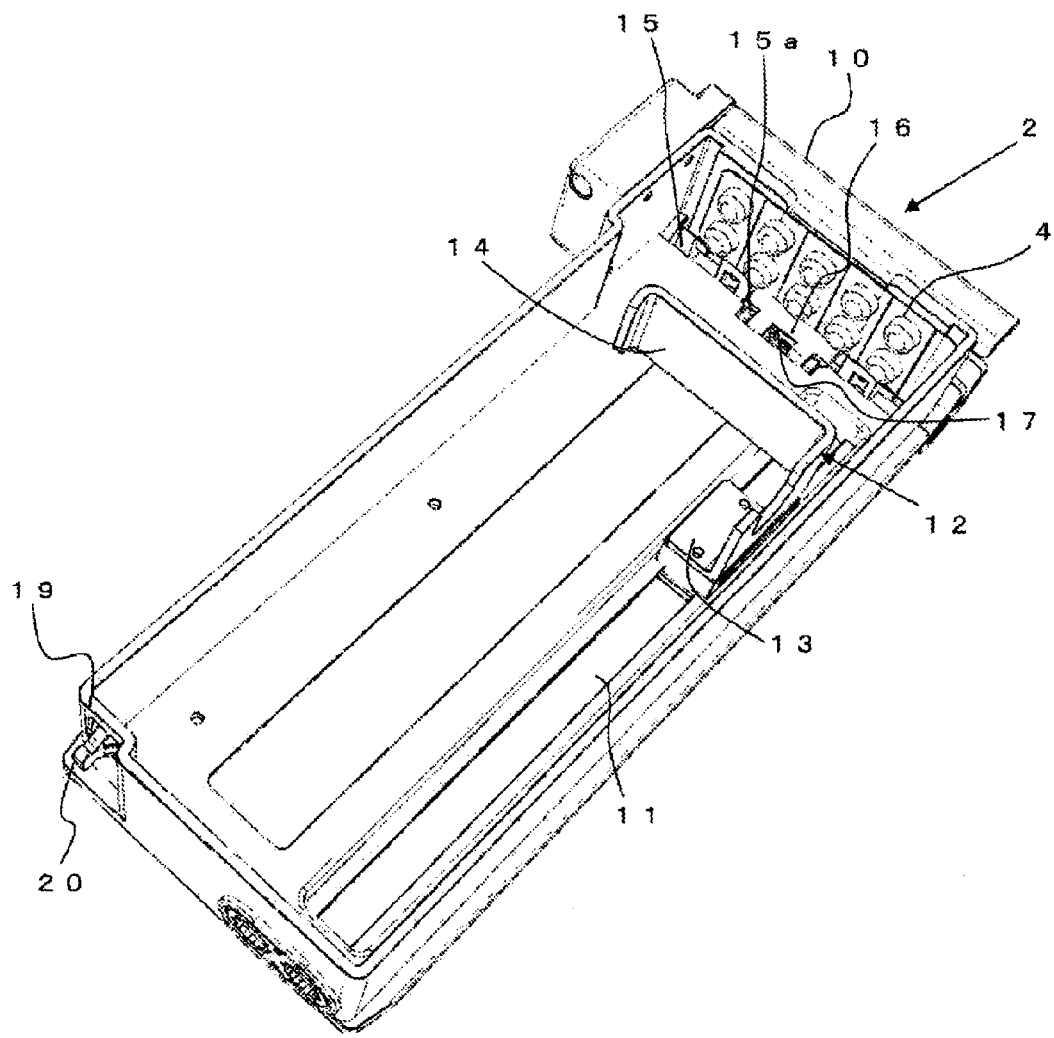
FIG. 3 is a perspective view of a cassette to be mounted on a cassette mount shown in FIG. 2.
Figure 4:
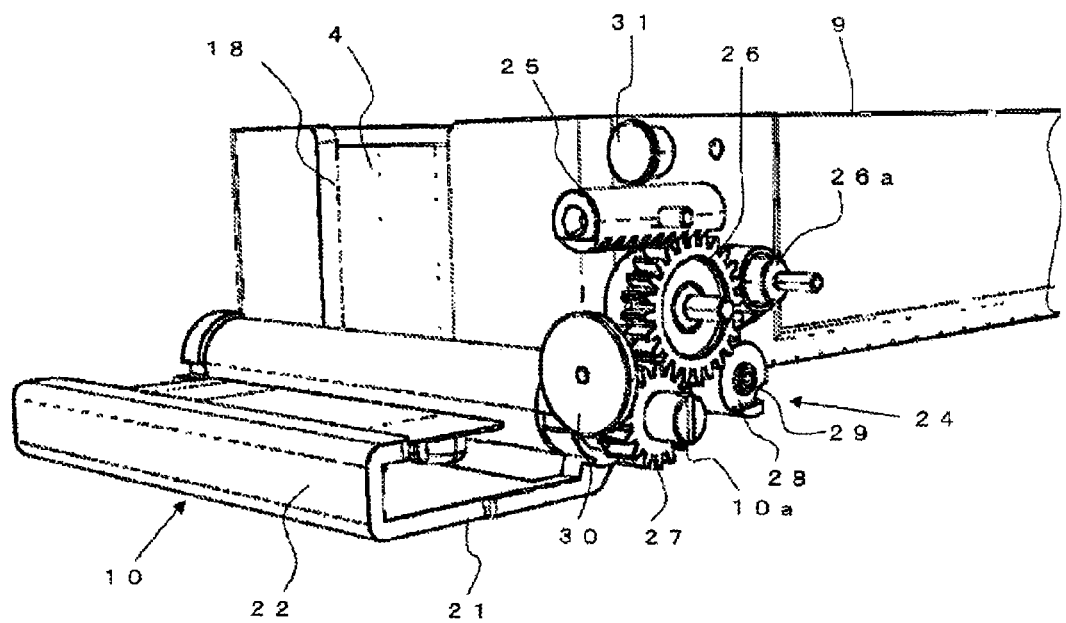
FIG. 4 is a fragmentary perspective view taken at another angle, showing that an opening/closing door is pivoted to a 90 degree opened position from FIG. 3 and a casing of a drive mechanism is removed.
Figure 5:
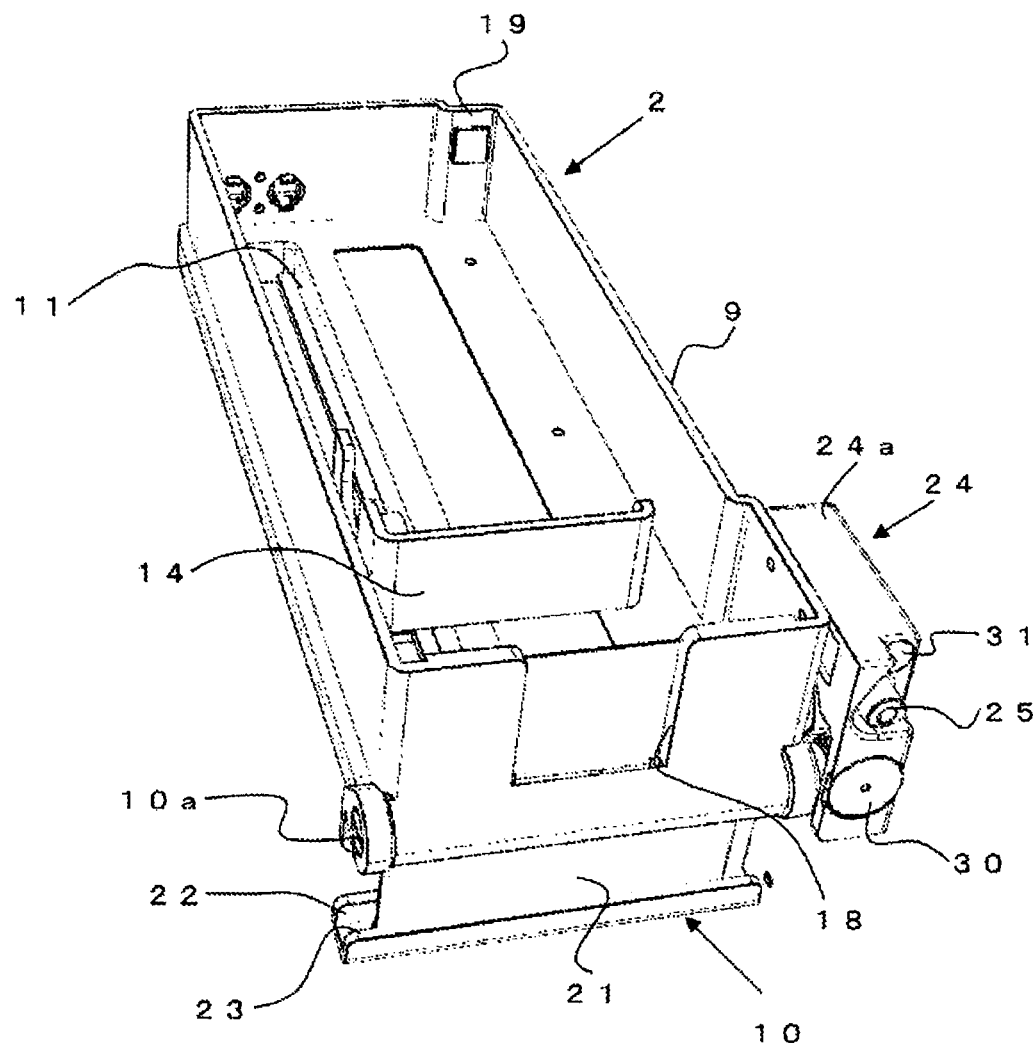
FIG. 5 is a perspective view taken at yet another angle, showing that the opening/closing door is pivoted to a 180 degree opened position from FIG. 3.

The cassette 2, as shown in FIGS. 3 to 5, includes a cassette body 9 of a generally rectangular parallelepiped shape with open top and an opening/closing door 10 disposed on the front of the cassette body 9.

Formed on a bottom surface of the cassette body 9 is a guide groove 11 that is alongside a sidewall opposite a projecting sidewall from front to back. An extruding member 12 is reciprocably disposed on the guide grove 12. The extruding member 12 includes a slide portion 13 sliding on the guide groove 11 and a pusher piece 14 extending from the slide portion to transverse the inside of the cassette body 9. A not-shown constant force spring (CONSTON) is housed in the slide portion 13 to bias the extruding member 12 toward the opening/closing door under a constant force regardless of the position of the slide portion 13.

Further, formed in a bottom front end of the cassette body 9 is a dispensing opening 15 that permits removal of the foremost blister pack 4 therethrough. The dispensing opening 15 is closed in part by a closure piece 16 pivotably provided at a cutout portion 15a of the bottom front end, thereby preventing the foremost blister pack 4 from falling down. The closure piece 16 is biased in its closure direction by a spring 17.

The front of the cassette body 9 is cut out at its central portion to thus define a communication portion 18. The communication portion 18 serves as a relief for allowing a push-down piece to move therein when removing the foremost blister pack 4 as described below.

A stepped portion 19 is formed in the rear of the cassette body 9. An engaging piece 20 is attached to an opening formed in the stepped portion. The engaging piece 20 removably engages an engaging receptor (not shown) when mounting the cassette 2 in the cassette mount 8 of the device body 1.

The cassette body 9 contains a plurality of the blister packs 4 (PTP (Press Through Package) sheet) as they are arranged one behind another in a transverse orientation. Although not shown in greater detail, the blister pack 4 includes a plurality of pocket portions for containing medicines therein and a cover film adhered thereto for sealing the pocket portions. The arrangement direction of the blister packs 4 is such that the cover film faces toward the front of the cassette body 9.

The opening/closing door 10 is pivotally provided about a spindle 10*a* provided in a front lower end of the cassette body 9. The opening/closing door 10 includes a front portion 21 extending from the spindle 10*a* and a guide portion 22 of generally U-shaped cross section that is bent from a front edge of the front portion 21. The guide portion 22 functions to retain the fraction (the remainder) of the blister pack 4. To this end, the guide portion is preferably constructed to have at least elasticity to retain the blister pack 4 (elastic supporter). By way of example of the elastic supporter, a rubber may be provided in one of the opposite surfaces defining the guide portion 22. A cutout portion 23 is formed midway in one side edge of the front portion 21. A gripping part (this will be described below) can grip the fraction of the blister pack 4 through the cutout portion 23.

The opening/closing door 10 is pivoted by a drive mechanism 24 provided in the front of one sidewall of the cassette body 9. The drive mechanism 24 is constructed such that pushing in a push bar 26 projecting from the front end surface of a casing 24*a* rotates, via a first gear 26, a second gear 27 meshing with the first gear 26, thus rotating the spindle 10*a* integrated with the second gear to pivot the opening/closing door 10. The opening/closing door 10 can be positioned to a closed position (see FIG. 3), a 90 degrees opened position (see FIG. 4) or a 180 degrees opened position (see FIG. 5) by changing the extent of pushing in the push bar 25. The first gear 26 is biased by a constant force spring 26*a* attached to a pin in a rotating direction of projecting the push bar 25. Further, the biasing force from the constant force spring maintains the opening/closing door 10 in the closed position. An engaging gear 28 capable of meshing with the first gear 26 is provided. The engaging gear 28 can engage and disengage from the first gear 26 in a manual manner by rotating a manipulation portion 29 projecting from a lateral side of the casing 24*a*. In the event that the opening/closing door 10 is positioned to the 90 degrees opened position or the 180 degrees opened position, or in the event that the opening/closing door 10 must not be opened when detaching the cassette 2 from the cassette mount 8, the engaging gear 28 is used to meshing with the first gear 26 in a manual manner.

A magnetic portion 30 is disposed in the front end surface of the casing 24*a*. When the cassette 2 is drawn out from the cassette mount 8, the magnetic portion 30 is attracted to a solenoid portion 42. Further, a light-emitting portion 31 is provided in the front end surface of the casing 24*a*. An LED (not shown) provided in the device body irradiates a light to the light-emitting portion. For example, when notifying exhaustion or abnormality of medicines, the LED irradiates the light-emitting portion 31. Such configuration can eliminate electrical parts or wiring from the cassette 2 and can simplify the structure thereof to thus allow for a low-cost manufacture.

Figure 6:
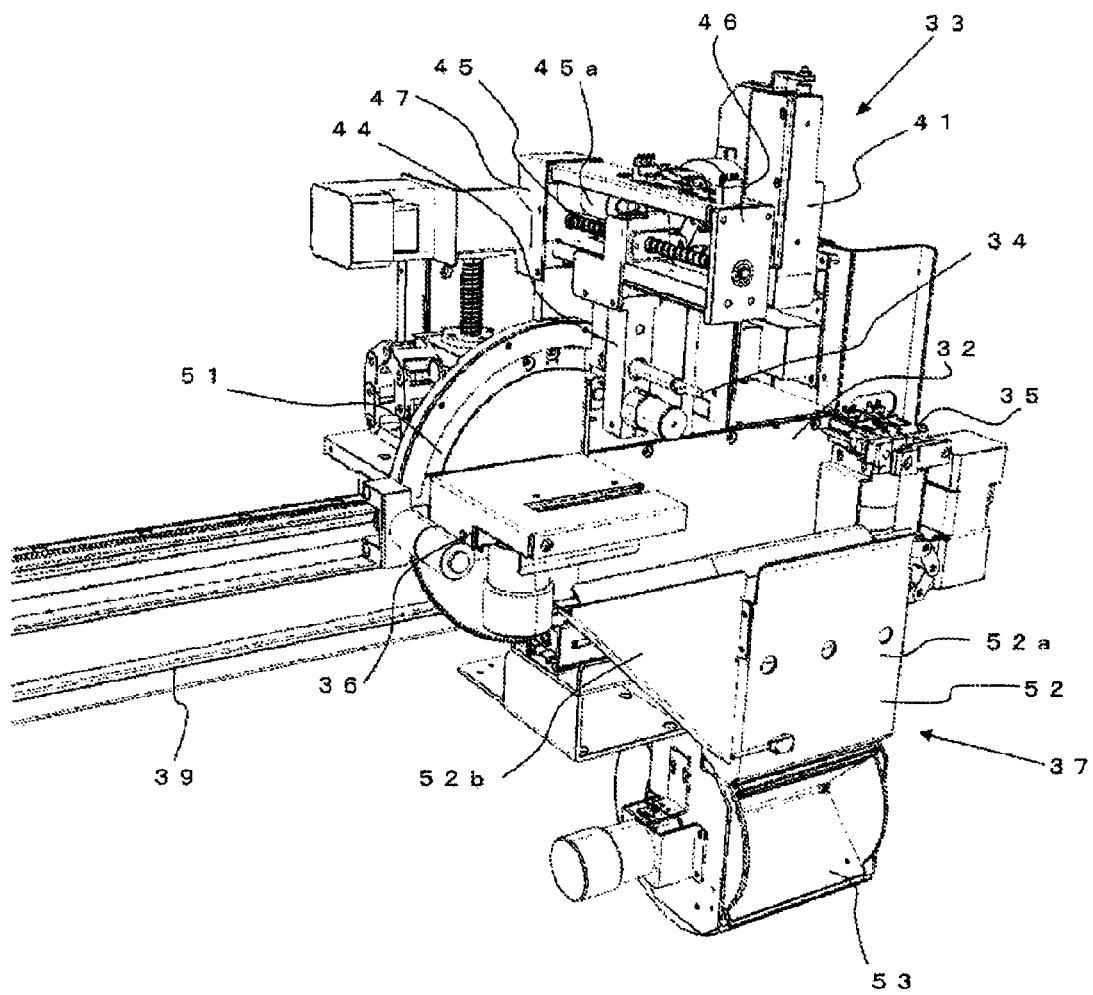
FIG. 6 is a perspective view showing a dispensing member shown in FIG. 1.
Figure 7:
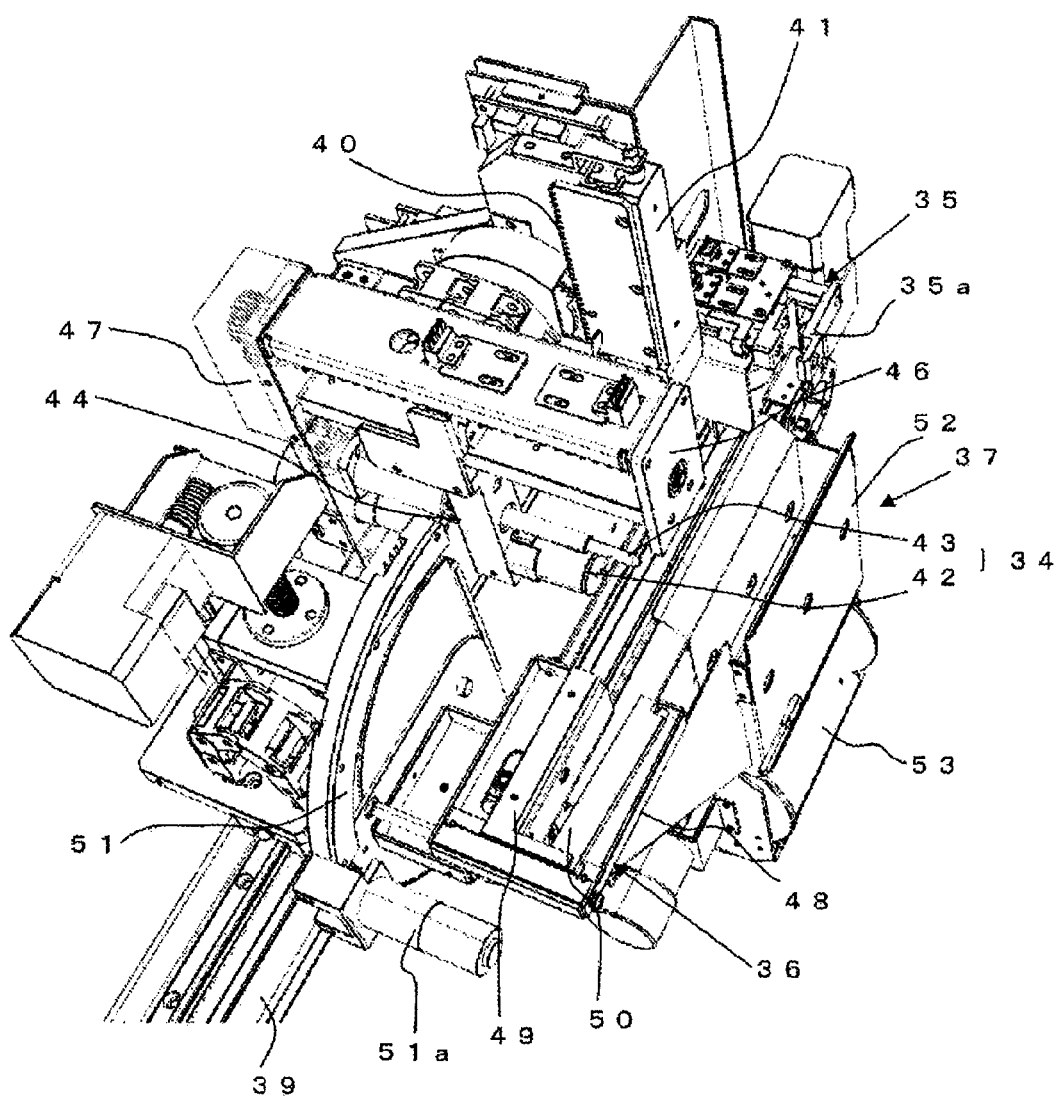
FIG. 7 is a perspective view taken at another angle from FIG. 6.

As shown in FIGS. 6 and 7, the dispensing member 3 includes a base 32, a first dispensing member 33, a second dispensing member 34, a gripping member 35, a cutting member 36 and a collecting member 37. The base 32 is reciprocably provided in a horizontal rail 39 that can be lifted and lowered with respect to vertical rails 38 disposed right and left in the front of the device body 1.

The first dispensing member 33 is constructed such that a rack 40 is in mesh with a gear provided in a rotating shaft of a motor and a push-down portion 41 integrated with the rack 40 is lifted and lowered by normal and reverse operation of the motor. A lower end of the push-down portion 41 pushes down the blister pack 4 that is located foremost in the cassette 2. Then, the blister pack is ejected through the dispensing opening 15 formed in the bottom front end of the cassette 2.

The second dispensing member 34 includes the solenoid portion 42 and a pusher 43. The solenoid portion 42 is anchored to a moving piece 44 and is excited by energization to attract a magnetic object. An upper end portion of the moving piece 44 is screw-engaged to a screw 45. The screw 45 is rotatably supported to a front plate 46 and a rear plate 47. Operation of a motor 45*a* rotates the screw 45 via a gear (not shown) and thus the solenoid portion 42 is reciprocated frontward and rearward via the moving piece 44. The solenoid portion 42 attracts the magnetic portion 30 of the cassette 2 in a forward position and is then retracted to draw out the cassette 2 from the cassette mount 8 to a medicine removal position. The pusher 43 is movable frontward and rearward (in a horizontal direction) by operation of a motor (not shown). The pusher pushes in the push bar 25 of the cassette 2. Further, by setting a position where the pusher 43 pushes in the push bar 25 to two stages, the opening/closing door 10 that is located in the closed position can be positioned to each of the 90 degrees opened position and the 180 degrees opened position.

The gripping member 35 includes a pair of gripping pieces 35*a* that are opened and closed by operation of a motor (not shown). The gripping member is recriprocably provided on a horizontal groove formed in the front of the base 32. The pair of the gripping pieces 35*a* grip the blister pack 4.

The cutting member 36 is constructed such that a fixed blade 49 and a movable blade 50 are attached to a supporter 48. The movable blade is horizontally reciprocated to move toward and away from the fixed blade 49. The supporter 48 is anchored to a fan-shaped rotating plate 51 (position adjusting member) at its one end surface. A gear, which is in mesh with a gear provided in a rotating shaft of the motor 51*a*, is formed on an outer periphery of the rotating plate 51. Normal and reverse operation of the motor 51*a* rotates the rotating plate 51 through the gear. Thus, the fixed blade 49 and the moving blade are rotated along with the rotating plate 51 to change a cutting position for the blister pack 4 gripped by the gripping member 35. In this embodiment, the cutting member 36 is positioned to two places of horizontal and vertical positions. Further, the cutting member 36 includes a lifting/lowering mechanism (not shown), thereby adjusting the cutting position made by the fixed blade 49 and the movable blade 50. Accordingly, the blister pack 4 with a plurality of rows can be cut into the fraction having one tablet at minimum. Further, preferably, a plate spring member for pressing the blister pack 4 before being cut by the movable blade 50 is provided in order to prevent positional shift (e.g., bounce) of the blister pack 4 due to impact during cutting.

The collecting member 37 includes a guide passage 52 and a collecting container 53. The guide passage 52 comprises a straight section 52*a* and a slope section 52*b*. The blister pack 4 that falls down from the dispensing opening 15 of the cassette 2 passes through the straight section 52*a*. The fraction of the blister pack 4 that is cut off by the cutting member 36 passes through the slope section 52*b* and then joins the straight section 52*a*. The collecting container 53 has three storage sections (not shown). The blister packs 4, which are supplied through the guide passage 52, are transferred to each partition partitioned in a tray (not shown) that is conveyed by the conveying device 7.

Operation

Next, descriptions will be provided as to the operations of the medicine dispensing device constructed as described above.

When a prescription data is inputted from the host computer (not shown), the dispensing member 3 is moved to the cassette 2 that contains the blister pack 4 having corresponding medicines.

Figure 8:
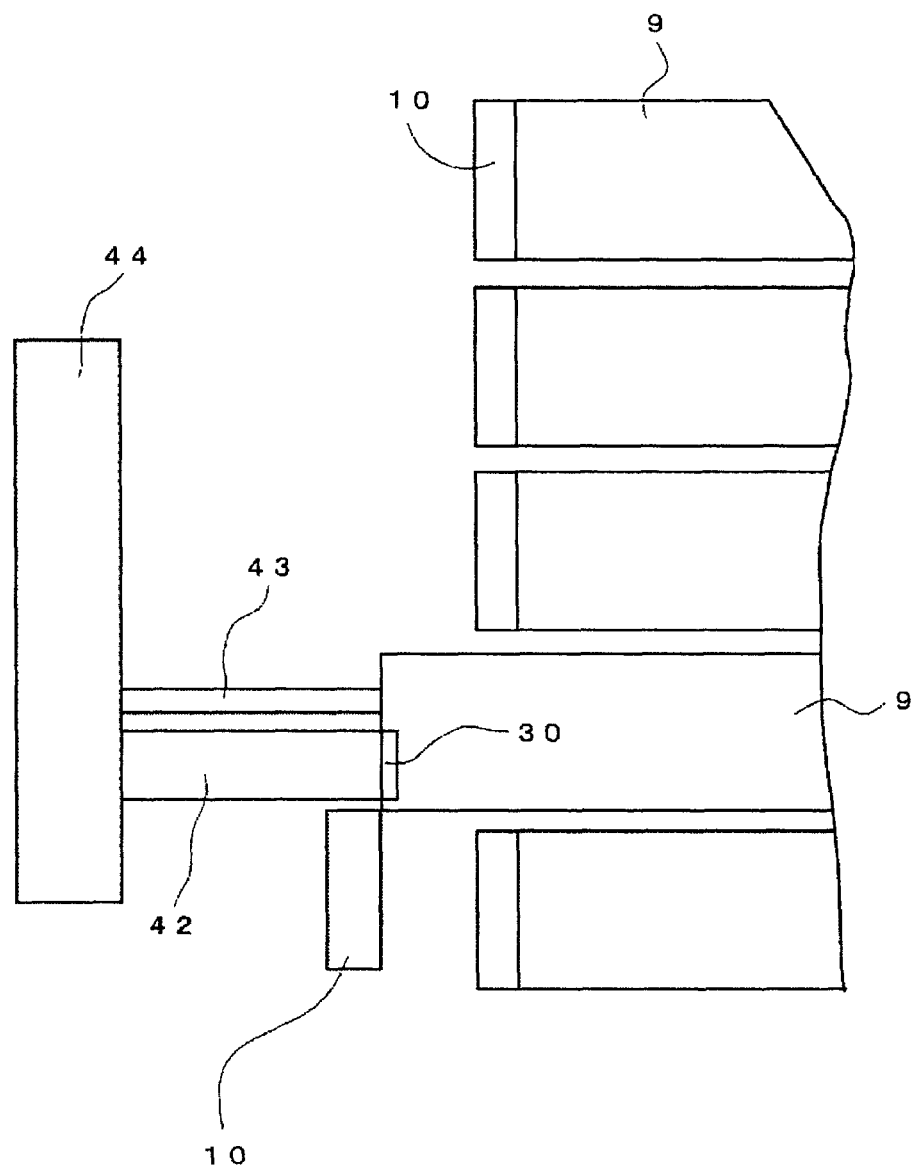
FIG. 8 is a schematic side view showing when a blister pack is removed from a cassette.

When dispensing the blister pack 4 per one sheet, the pusher 43 is advanced by the operation of the motor and the solenoid portion 42 is excited. As a result, the magnetic portion 30 of the cassette 2 is attracted. Then, the pusher 43 is retracted and thereby the cassette 2 is positioned to the medicine dispensing position, as shown in FIG. 8. At this state, the push bar 25 of the cassette 2 is pushed in. The pushing extent in this case is such that the opening/closing door 10 is pivoted until the 90 degrees opened position. As a result, the communication portion 18 in the front end surface of the cassette body 9 is exposed, such that the push-down portion 41 of the dispensing member 3 can push down the blister pack 4 located foremost. In such a state, as the push-down portion 41 is moved downwardly via the gear and the rack 40 by the operation of the motor, the blister pack 4 located foremost pivots the closure plate against the biasing force of the spring 17 and is ejected from the cassette 2 through the dispensing opening 15. The ejected blister pack 4 passes through the guide passage 52 and is then collected in the colleting container 53. If the blister pack 4 is collected in the collecting container 53, then the solenoid portion 42 is advanced to place the cassette 9 in the cassette mount 8. Subsequently, the solenoid portion 42 is de-excited to stop attracting the magnetic portion 30 and thereafter the collecting container 53 (dispensing member 3) is moved to the tray (not shown). Further, when dispensing a plurality of the blister packs 4, the push-down operation of lowering the push-down portion 41 and the return operation of lifting the push-down portion are repeated.

When dispensing the blister pack 4 in fraction, the extent of pushing in the push bar 25 is such that the opening/closing door 10 is pivoted until the 180 degrees opened position. In such a state, similarly to the foregoing, the push-down portion 41 pushes down the blister pack 4 located foremost. Then, the blister pack 4 is ejected through the dispensing opening 15 and is held in the guide portion 22 of the opening/closing door 10. In this state, the gripping member 35 is driven to grip the blister pack 4 through the cutout portion 23 formed in the guide portion 22. Subsequently, the gripping member 35 is horizontally moved to move the gripped blister pack 4 to the cutting member 36. The cutting member 36 changes its rotation position according to the fraction of the blister pack 4.

When the pocket portions of the blister pack 4 are arranged in a even number row (two rows or four rows), if the fraction is a number, then the cutting member 36 is pivoted at 90 degrees to thereby be set to the vertical position and the position of the gripping member 35 is adjusted, thereby positioning the blister pack so that a portion to be cut off can include a desired quantity. Thereafter, if the blister pack 4 is cut by the cutting member 36, then only the desired fraction passes through the guide passage 52 and is collected in the collecting container 53.

Further, if the fraction is an odd number, then the blister pack 4 is cut as explained above and thereafter one remaining piece is cut from the remainder of the blister pack 4. In this case, the remainder of the blister pack 4 may be cut widthwise by a half from its edge. Thereafter, the rotating plate 51 is rotated at 90 degrees to thereby be set to the horizontal position and the remainder may be cut by a further half.

When the pocket portions of the blister pack 4 are arranged in an odd number row (three rows), the processes opposite to the foregoing may be performed for both the even number fraction and the odd number fraction.

The remainder of the blister pack 4, the fraction of which is cut off as explained above, is carried to the guide portion 22 of the opening/closing door 10 by the movement of the gripping member 35. Then, the gripping member 35 releases the grip and the remainder of the blister pack 4 is supported by the elastic supporter provided in the guide portion 22. In such a case, the supporting position made by the elastic supporter may be stored as a coordinate data together with a remaining quantity (the number of the pocket portions). Further, in next dispensing, the gripping member 35 may be moved based on such a data to dispense the remainder of the blister pack 4. Further, where the remainder of the blister pack 4 retained in the guide portion 22 is absent, a new blister pack 4 may be ejected from the cassette 2 to the guide portion 22 and then cut as explained above.

Another Embodiment

The present invention should not be limited to the foregoing embodiment. Various variations and modifications may be made within the subject matter of the claims.

Second Embodiment

For example, the closure piece 16 is provided in the dispensing opening 15 of the cassette 2 in order to prevent the blister pack 4 from falling down. The closure piece 16 may be configured as shown in FIG. 9. Referring to FIG. 9, the closure piece 16 is fixed to the bottom surface of the cassette body 9. Further, its leading edge is shaped concavely and convexly in accord with the contour of the pocket portions of the blister pack 4 to be located thereto. Thus, in the blister packs 4 contained in the cassette 2, only the foremost one can fall down through the gap formed near the leading edge of the closure piece 16. However, since the blister packs 4 contained in the cassette 2 are biased by the constant force spring, they do not fall down through the gap. When the foremost blister pack 4 is forcedly pushed down by the push-down piece, only the blister pack located foremost is ejected from the dispensing opening 15, while the second or more blister packs 4 are prevented from moving by the closure piece 16. Further, the leading edge of the closure piece 16 has a circular arc cross-section from a top surface toward a bottom surface. Thus, jamming is difficult to occur when the blister pack 4 is ejected.

Third Embodiment

According to the foregoing embodiment, the position of the cutting member 36 relative to the blister pack 4 gripped by the gripping member 35 is changed through the rotation of the rotating plate 51. However, the position of the blister pack 4 gripped by the gripping member 35 relative to the cutting member 36 may be changed through the rotation of the gripping member 35 or the rotation of both the cutting member 36 and the gripping member 35.

Fourth Embodiment

According to the foregoing embodiment, the opening/closing door 10 is opened and closed by the drive mechanism 24 provided in the front of the one sidewall of the cassette body 9. However, as shown in FIGS. 10 to 14, the first dispensing member 33 may be constructed to have such a function.

Figure 10:
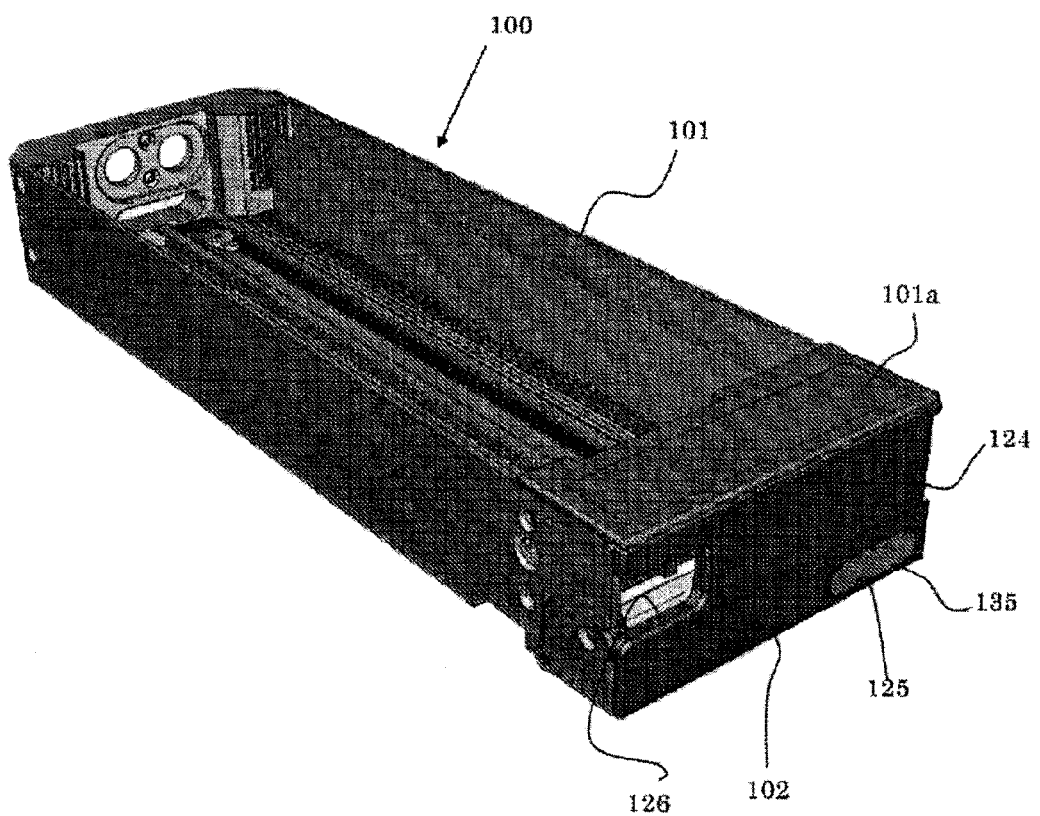
FIG. 10 is a perspective view of a cassette in accordance with a fourth embodiment.
Figure 11:
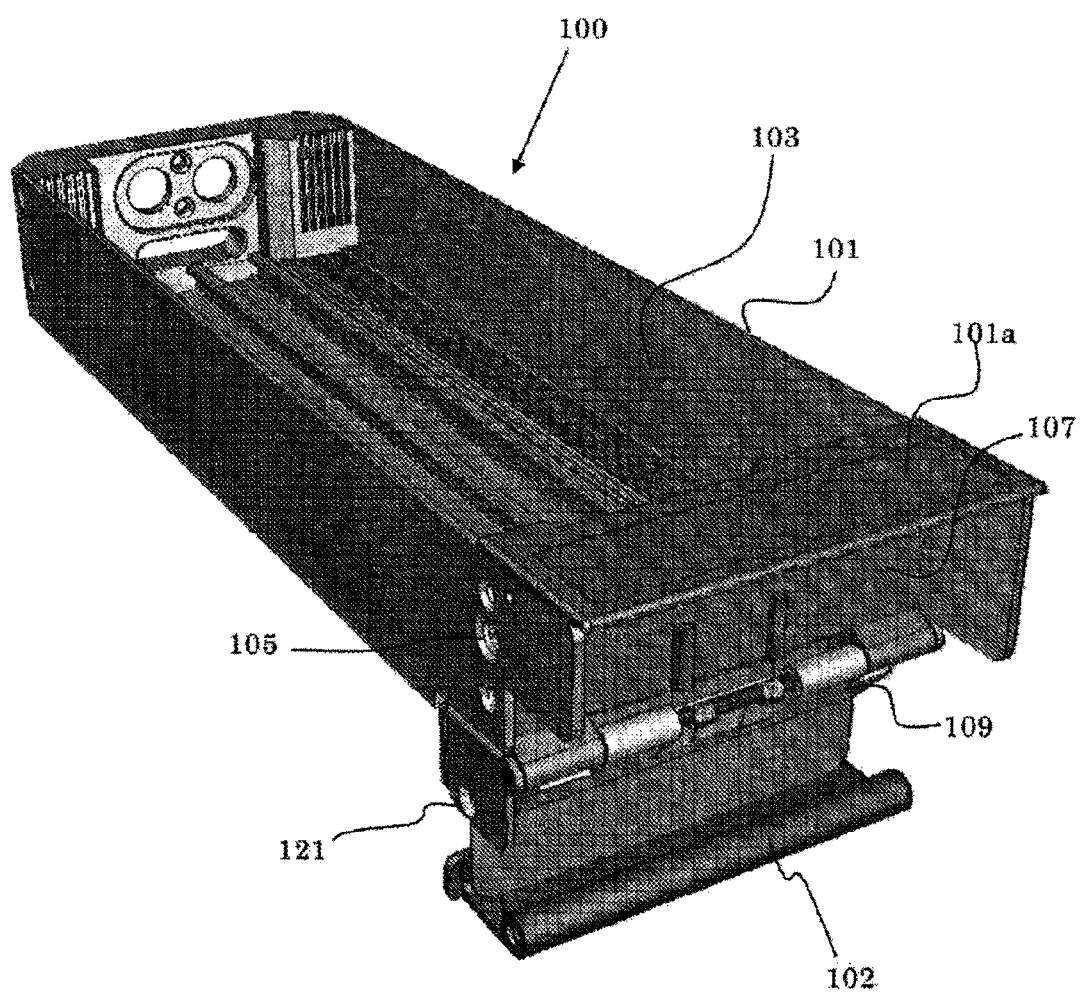
FIG. 11 is a perspective view showing that an opening/closing door is pivoted to an opened position from FIG. 10.
Figure 12:
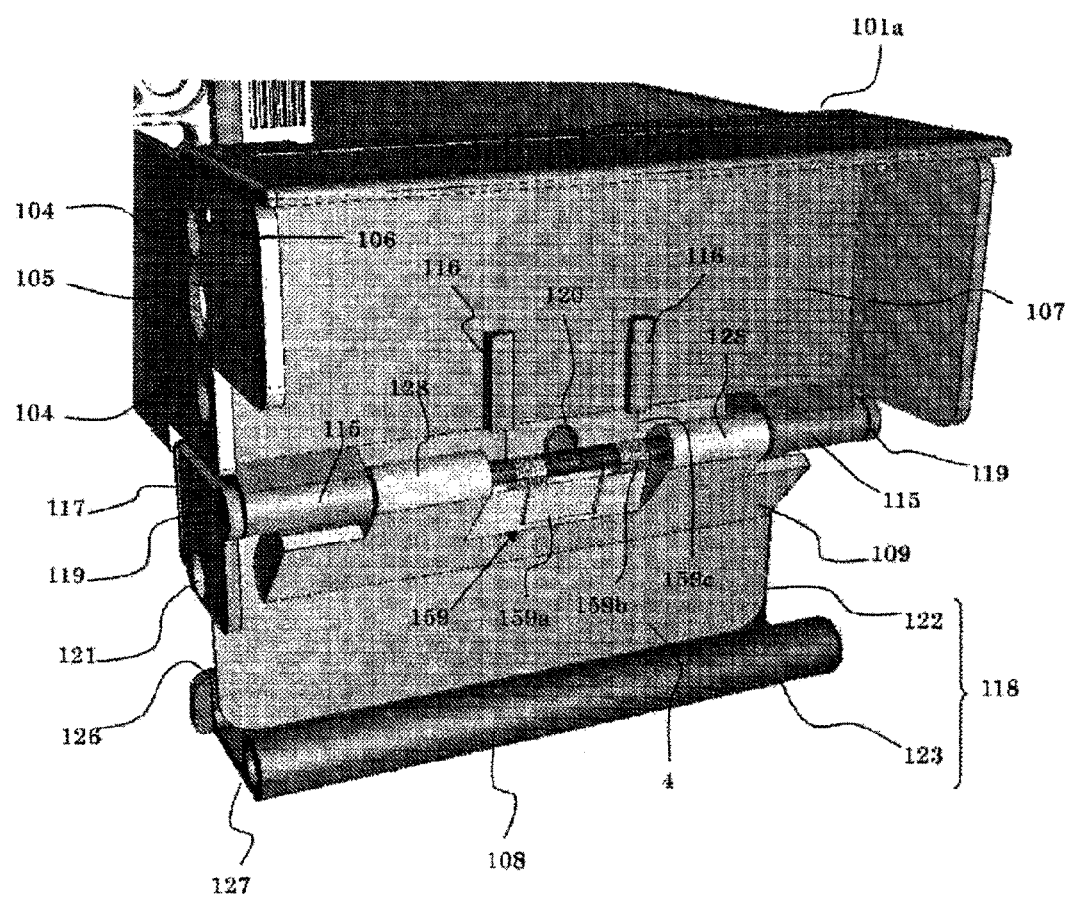
FIG. 12 is an enlarged view showing the vicinity of the opening/closing door.

Specifically, the cassette 100 shown in FIGS. 10 to 12 includes a cassette body 101 and an opening/closing door 102 disposed in the front of the cassette body.

The cassette body 101 has a box-like shape with open top. An extruding member 103 containing a constant force spring 103 (CONSTON) is provided in the cassette body. The extruding member biases the blister packs 4, which are arranged one behind another in the cassette 100 similar to FIG. 9, toward the opening/closing door 102 under a constant force. Through apertures 104 for attaching a door body 107 of the opening/closing door 102 are formed up and down in each of both front sides of the cassette body 101. Further, a guide aperture 105 is formed between both the through apertures 104 and an engaging aperture 106 is formed near the upper through aperture 104.

Upper edges of the front sides of the cassette body 101 are connected to each other via a top plate 101a. According to such construction, when the opening/closing door 102 is positioned to a closed position as described below, the top plate 101a can cover the top surface of the opening/closing door. This can prevent the opening/closing door 102 from being opened unintentionally when the user manually draws out the cassette body 101. Further, a depression is formed on the top plate 101a and a label with the name, the quantity of tablets, etc. of the blister pack 4 printed thereon may be adhered to the depression.

The opening/closing door 102 includes the door body 107, an opening/closing member 108 and a pressure plate 109.

Figure 13:
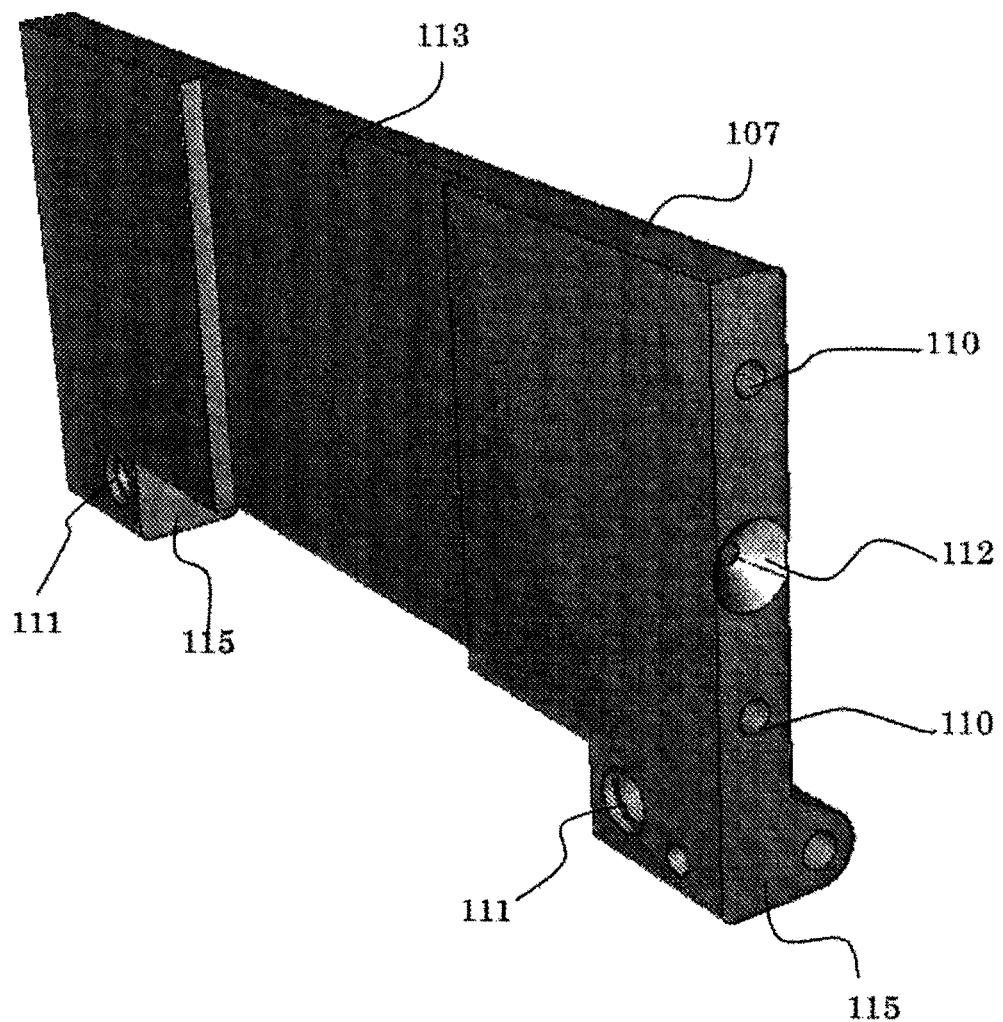
FIG. 13 is a perspective view showing a door body shown in FIG. 12.

As shown in FIG. 13, the door body 107 is a plate having a rectangular shape in a plan view. Threaded holes 110, to which screws are screw-engaged through the through apertures 104 formed in the cassette body 101, are formed up and down in both sides of the door body. A communication opening (not shown) is formed in the door body between the door body 107 and the bottom front end of the cassette body 101. The communication opening permits the blister pack 4 to pass therethrough when the door body 107 is attached to the cassette body 101. Further, a guide recess 112, which has a conical surface gradually deeper toward its center, is formed between the threaded holes 110 so as to correspond to the guide aperture 105. A relief groove 113 is formed on a central portion of a back of the door body 107. The relief groove allows the push-down piece 41 (see FIGS. 14 and 15) to move therein, when removing the foremost blister pack 4.

Further, a door body bearing portion 115 is formed in each of the lower side portions of the door body 107. As shown in FIG. 12, a spindle 120 is held in the door body bearing portion 115 and the opening/closing member 108 is pivotally attached to the spindle 120. Turning back to FIG. 13, a retaining recess 111 is formed in each of backs of the door body bearing portions 115. A ball plunger (not shown) is attached to each of the retaining recesses. The ball plungers abut a lower edge of the blister pack 4 pushed against the door body 107, thus preventing the blister pack from falling down through the communication opening. Further, while not shown, pins (not shown) project forward in two places from a bottom front end surface of the cassette body 101. When the blister pack 4 pushed against the door body 107 is pushed down by a push-down piece 114 and passes through the communication opening, these pins prevent the blister pack 4 located next from moving together with the former blister pack.

Further, as shown in FIG. 12, protrusion claws 116 are formed in the front central portion of the door body 107 widthwise at a predetermined interval. These protrusion claws have insertion holes at lower ends. Leg sections 159c of both ends of a spring 159 (this will be described below) are inserted to the respective insertion holes.

As shown in FIG. 12, the opening/closing member 108 includes an opening/closing supporting portion 117 and an opening/closing plate 118. The opening/closing member can be pivoted to the following positions: a closed position (see FIG. 10) where the opening/closing member is positioned on the front of the cassette body 101; a first opened position where the opening/closing member is pivoted at 90 degrees from the closed position and the blister pack 4 is dispensed as it is; and a second opened position (see FIG. 11) where the opening/closing member is pivoted perpendicularly downwardly and a fraction is cut off from the blister pack 4 and is dispensed.

The opening/closing supporting portion 117 is formed of a magnetic material. The opening/closing plate 118 is attached to the opening/closing supporting portion. Arm portions 119 bent at a right angle extend from both ends of the opening/closing supporting portion. Leading ends of the arm portions 119 are pivotally connected to the door body 107 about the spindle 120. One of the arm portions 119 expands to have the same width as that of an attach plate 135. A manipulation aperture 121 is formed in such an expanding portion of the arm portion.

The opening/closing plate 118 of generally L-shaped cross-section includes a first flat portion 122 and a second flat portion 123 that form the back and the bottom of the opening/closing door 102 respectively. As shown in FIG. 10, a depression 124 is formed in the first flat portion 122 (e.g., in a surface frontally located in the closed position). A label with the name, the quantity of tablets, etc. of the blister pack 4 to be contained in the cassette 100 appropriately printed thereon is adhered to the depression 124. An opening 125 for exposure of a portion of the attach plate 135 is formed near the depression 124. Thus, the solenoid portion 42 (see FIG. 14), which is provided in the first dispensing member 133 and can be advanced and retracted, attracts the portion of the attach plate 135 exposed through the opening 125 and thus the cassette 100 can be pulled and drawn out from a shelf. Further, a detecting sensor (not shown) provided near the solenoid portion detects whether the cassette 100 can be pulled out and drawn out by the solenoid portion 42 or not. Further, a cutout portion 126 is formed in a side of the first flat portion 122. The cutout portion 126 is used when the gripping member 35 grips the remainder of the blister pack 4 with the fraction cut off. Meanwhile, the second flat portion has a shaft-shaped leading edge. Engaging protrusions (ball catch) 127 are formed at both lateral ends of the leading edge. The engaging protrusions 127 engage and disengage from the engaging apertures 106 formed in the both front sides of the cassette body 101 and, when engaging the engaging aperture, position the opening/closing member 108 to the closed position with respect to the cassette body 101.

As shown in FIG. 12, as for the pressure plate 109, pressure plate bearing portions 128 provided at a predetermined interval are pivotally supported to the spindle 120 exposed between the door body bearing portions 115. The pressure plate 109 is biased by the spring 159 and sandwiches the remainder of the blister pack 4 with the fraction cut off between the pressure plate and the first flat portion 122 of the opening/closing plate 118.

The spring 159 includes the following: a generally U-shaped section 159a placed into pressure contact with the pressure plate 109; coiled sections 159b connected to both ends of the U-shaped section and encircling the spindle 120 exposed between the pressure plate bearing portions 128; and the leg sections 159c connected to ends of the coiled sections and inserted to the insertion holes of the protrusion claws 116 of the door body 107. Since the spring 159 constructed as such is used, the sandwiched state of the blister pack 4 caused by the pressure plate 109 changes depending upon the pivoting position of the opening/closing member 108. That is, when the opening/closing member 108 is positioned to the closed position, the sandwiched state becomes strongest. This can stabilize the sandwiched state of the blister pack when the remainder of the blister pack 4 with the fraction cut off therefrom is not used. Furthermore, when the opening/closing member 108 is positioned to the opened position, a force of sandwiching the blister pack becomes weakest (however, the second flat portion 123 of the opening/closing plate 118 is located under the sandwiched blister pack 4 and thereby the blister pack does not fall down). Accordingly, the gripping member 35 can easily grip and move the blister pack 4.

Fifth Embodiment

Figure 14:
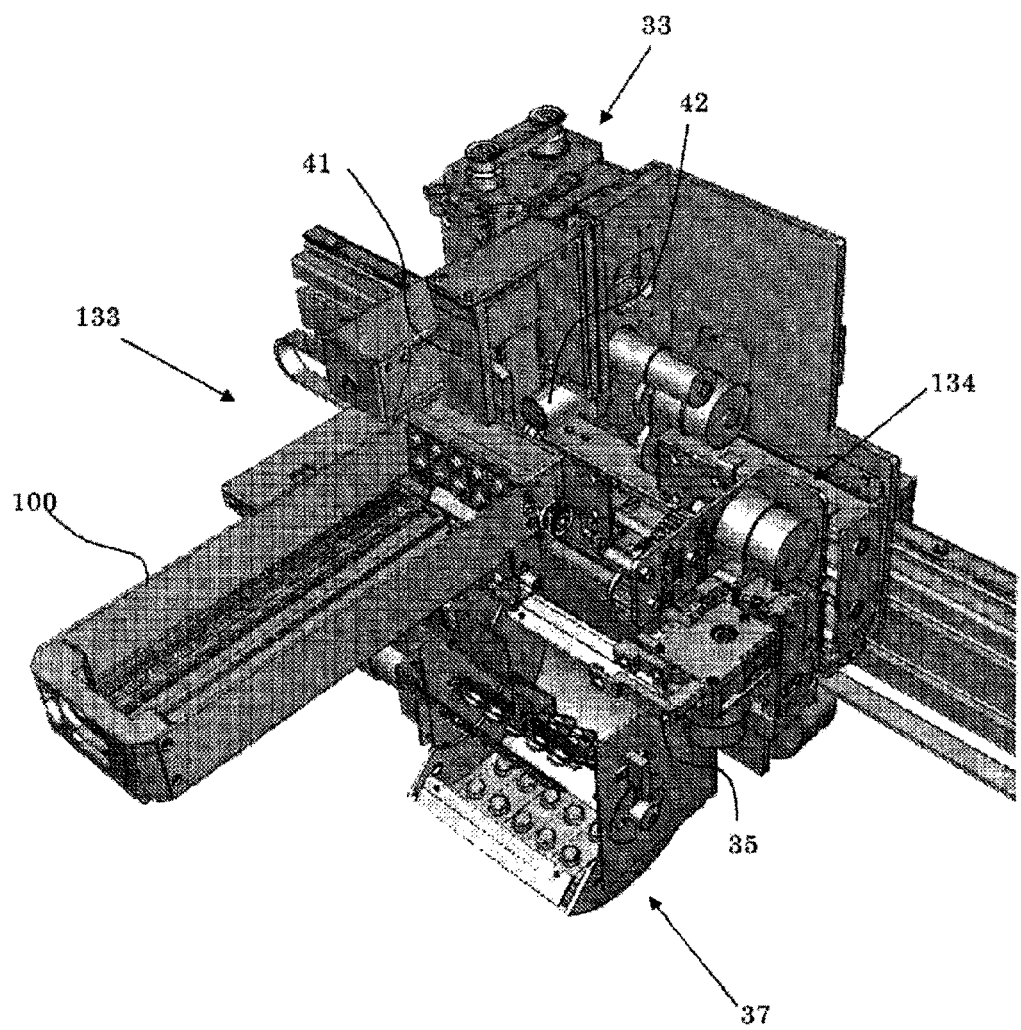
FIG. 14 is a perspective view showing a first dispensing member in accordance with a fifth embodiment.

The first dispensing member 133 shown in FIG. 14 includes a drive mechanism 134 for pivoting the opening/closing door 102 in addition to the configuration described in the foregoing embodiments. Descriptions provided below will be focused on the drive mechanism 134. As to the other configuration, like reference numerals are used and descriptions related thereto will be omitted.

Figure 15:
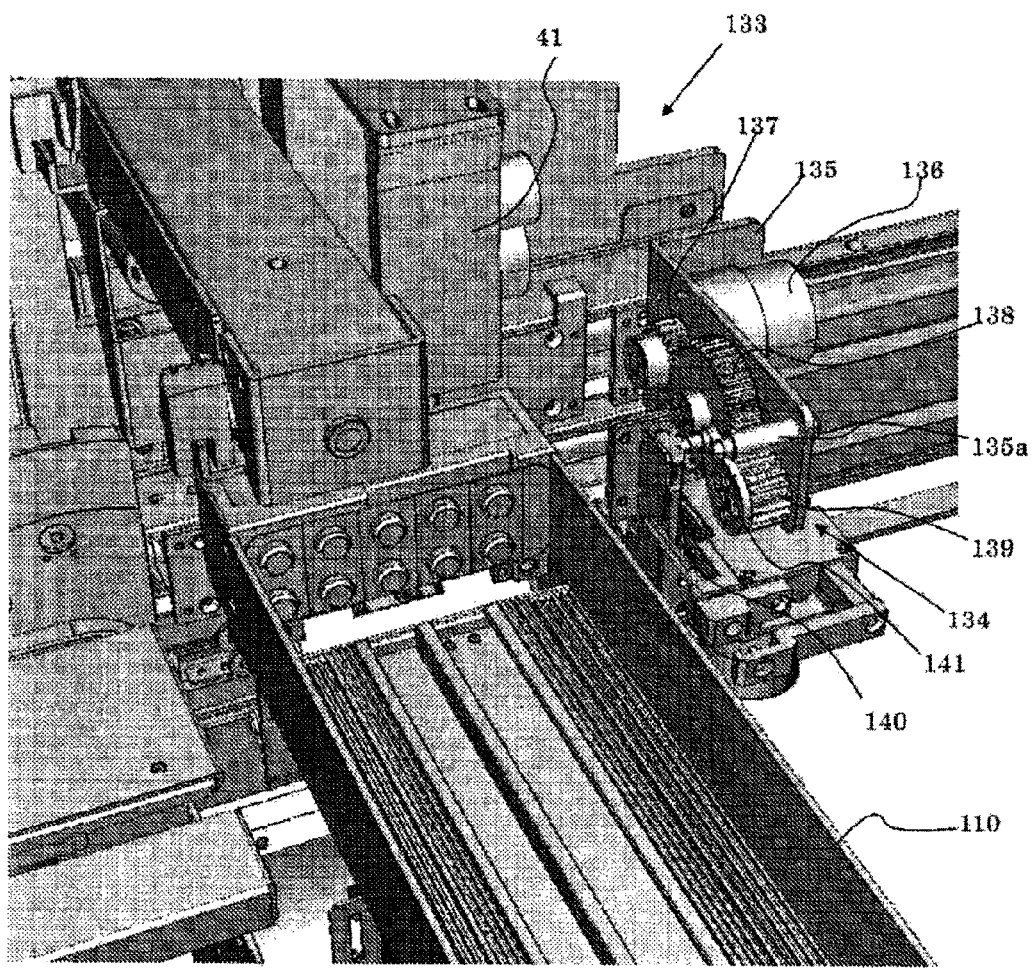
FIG. 15 is an enlarged fragmentary perspective view taken at another angle from FIG. 14.

As shown in FIG. 15, the drive mechanism 134 is constructed to transmit a drive power of a motor 136 provided in an attach plate 135 to a pivot pin 140 via gears. Further, the drive mechanism is constructed to be slidable in a width direction according to the sizes of the cassettes 100. In this embodiment, the drive mechanism can be positioned to three guide positions and one retraction position according to three types of differently sized cassettes 100.

Details of the drive function 134 are as follows. Specifically, a drive gear 137 is provided in a rotating shaft of the motor 136 and an intermediate gear 138 is in mesh with the drive gear 137 and a driven gear 139 is in mesh with the intermediate gear 138. A driven plate 141 with the pivot pin 140 is integrated with an end face of the driven gear 139. A leading end of the pivot pin 140 is positioned to the manipulation aperture 121 formed in the opening/closing supporting portion 117 (one of the arm portions 119) of the opening/closing member 108. Further, a guide pin 135a, which is positioned to the guide aperture 105 of the cassette body 101 and the guide recess 112 of the door body 107, is integrated with the attach plate 135. A leading end of the guide pin 135a is conically shaped for easy insertion to the guide aperture 105 and abuts a conical receptor surface of the guide recess 112. If the motor 136 is normally or reversely operated while the guide pin 135a is positioned to the guide aperture 105 as well as the guide recess 112 and the pivot pin 140 is positioned to the manipulation aperture 121, then the driven plate 141 (i.e., the pivot pin 140) is pivoted via the gears. Thus, the opening/closing member 108 is pivoted about the spindle 120 between the closed position and the opened position as positioned by the guide pin 135a. Preferably, a torque limiter may be provided anywhere in a power transmission path running from the motor 136 to the driven plate 141 (e.g., the rotating shaft of the driven gear 139). This may not apply a load to the cassette much than is necessary and thus prevent damages to the cassette when the drive mechanism 134 pivots the opening/closing door 102 to the closed position.

Figure 16:
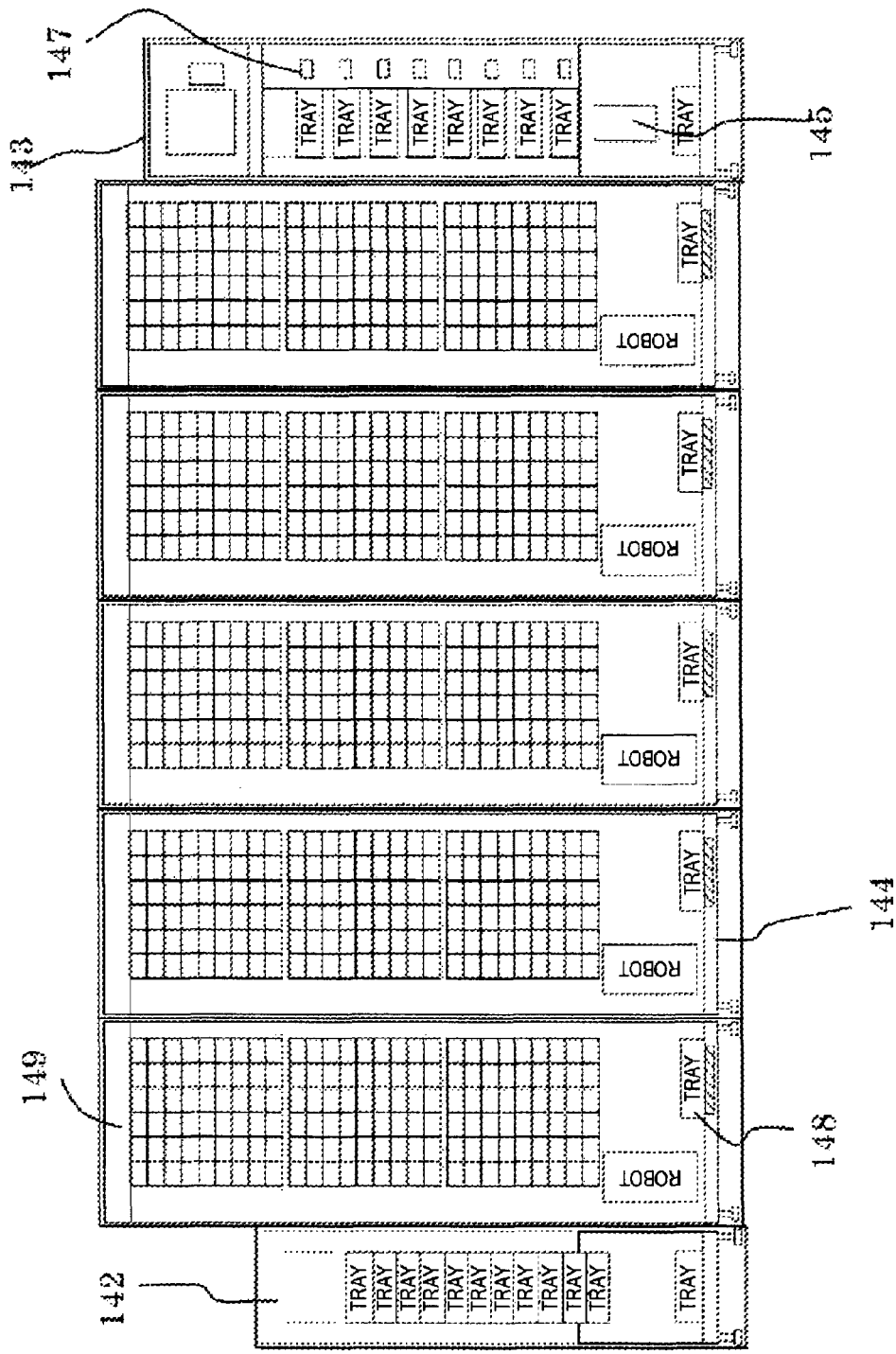
FIG. 16 is a schematic front view showing when a plurality of medicine dispensing devices according to one embodiment are arranged side by side and a tray feeding unit and a tray stacking unit are disposed at both sides.

The medicine dispensing device constructed as described above may be used alone. Further, as shown in FIG. 16, a plurality of the medicine dispensing devices may be provided side by side. Further, a tray feeding unit 142 and a tray stacking unit 143 may be disposed at both lateral sides respectively. In this case, a conveyance line 144 (e.g., belt conveyor) may be provided in a lower portion.

Figure 17:
FIG. 17 shows an indication slip printed by a journal printer provided in the tray stacking unit shown in FIG. 16.

A plurality of empty trays 148 are stacked one above the other in the tray feeding unit 142. The tray feeding unit feeds the trays to the conveyance line 144 one after another from the lowermost tray 148. The tray 148 fed to the conveyance line 144 is conveyed to the medicine dispensing device 149 and corresponding medicines are dispensed in the medicine dispensing device based on the prescription data. The tray 148 with the dispensed medicines therein is further conveyed to the tray stacking unit 143. In the tray stacking unit, a journal printer 145 supplies a paper (indication slip 146) shown in FIG. 17, on which the specification (prescription data) related to the dispensed medicines is printed, to the tray. Thereafter, the tray is conveyed upwardly in the tray stacking unit 143. As the tray 148 is conveyed upwardly and positioned in place, a LED 147 corresponding to such a place is turned on to notify that dispensing medicines to the tray 148 is finished. Further, instead of the LED 147, a liquid crystal panel may be used to display a patient's name.

Moreover, when dispensing all the medicines indicated by the prescription data is not finished due to shortage in the medicines, the tray stacking unit 143 turns on the LED 147 in another color or displays letters such as "MANUAL" to notify that some medicine is lacking and the user needs to manually feed it. Further, as for the medicines that cannot be dispensed in the medicine dispensing device, the indication slip 146, which is printed by the journal printer 145 and dispensed to each tray 148, may be printed in such a manner that such medicines are printed to be distinguishable from other medicines (e.g., such medicines are printed with red letters and other medicines are printed with black letters). That is, in the event that the blister packs 4 run short in the cassette 100, and that a manually-dispensed medicine (i.e., a medicine that cannot be set to the medicine dispensing device 149 and therefore needs to be dispensed by means of human hands) is present, the LED 147 and the indication slip 146 notify such a situation since the user (pharmacist) needs to feed such medicines.

Thus, when the pharmacist replenishes the tray 148 with medicines, the tray 148 associated with the LED 147 turned on may be removed. Also, the medicines, the names of which are printed with red letters in the indication slip 146, may be manually supplied, thereby reliably preventing the missing of the prescription. Further, a barcode is printed on the indication slip 146. When the barcode is read by a barcode reader, it can be stored in a memory inside a PDA (Personal Digital Assistant). Further, a screen of a PDA can display the insufficient medicines in the prescription data through communication with a server. When replenishing the tray 148 with medicines, the barcode of the indication slip 146 as well as a barcode of a medicine box accommodating medicines to be supplied may be read for purposes of checking errors in supplying the medicines. Accordingly, when replenishing the tray 148 with medicines through human hands, it is possible to record the matters associated with replenishment and further to manage all of medicine dispensing records (traceability) together with dispensing records in the medicine dispensing device 149.

Sixth Embodiment

Figure 18:
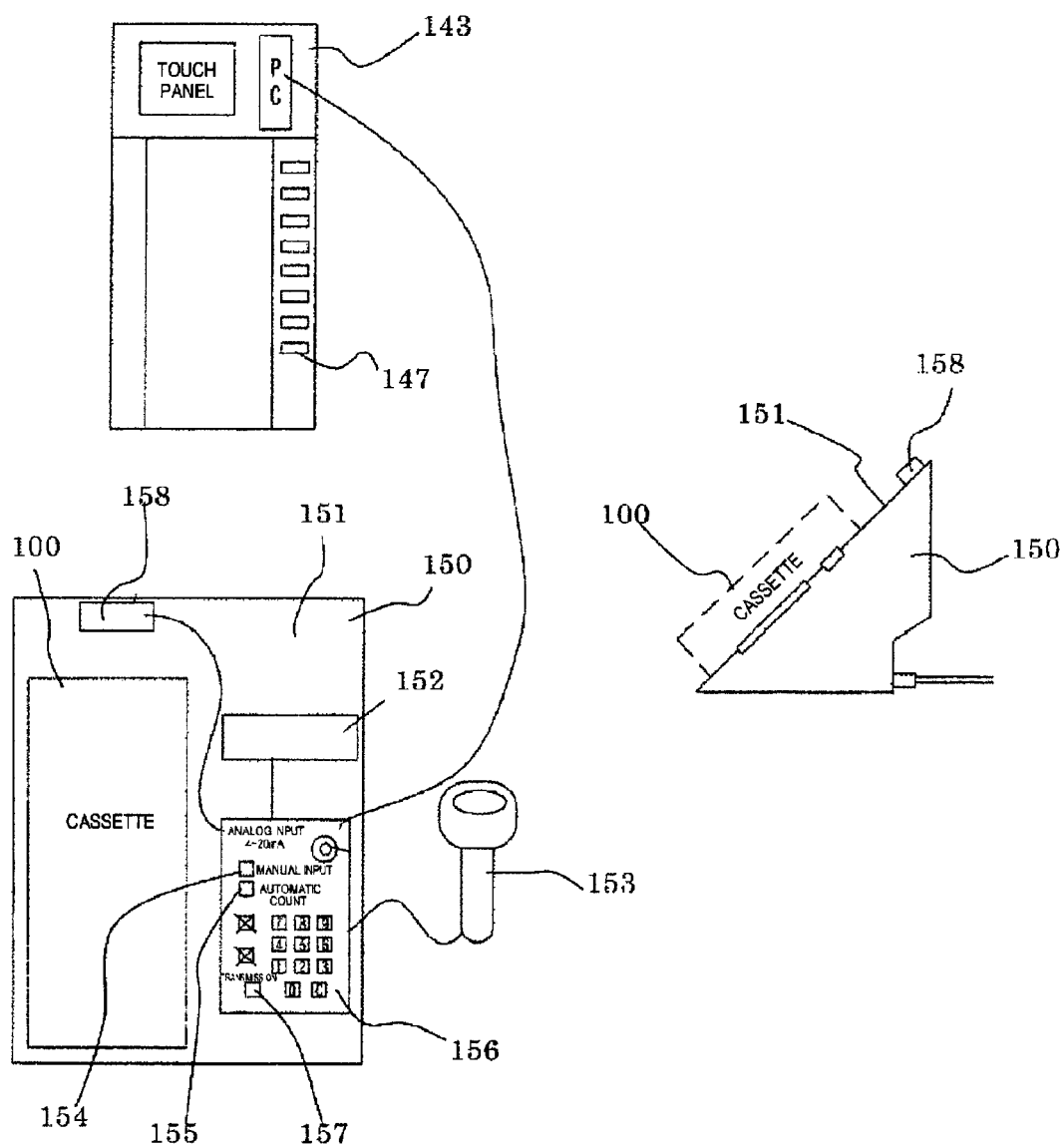
FIG. 18 schematically illustrates a filling unit for filing a cassette with blister packs, the cassette being mounted in a medicine dispensing device according to a sixth embodiment.

As shown in FIG. 18, replenishment for insufficient medicines may be preferably performed by means of a dedicated filling unit 150. The filling unit 150 includes a slope surface 151. The cassette 100 is placed on the slope surface 151 with its front facing downwardly. A display panel 152 is provided on an upper portion of a right half of the slope surface 151. When the barcode of the medicine box accommodating the medicines to be supplied is read by a barcode reader 153, the name of the medicine is displayed in an upper section of the display panel 152. Further, when a barcode for recognition of the medicine type on a label adhered to a medicine bottle from a pharmaceutical company is read by the barcode reader 153, the name of the medicine for replenishment is displayed on a lower section of the display panel 152. The user compares the names of the medicines and, if coincident, manipulates a "MANUAL INPUT" button 154 or an "AUTOMATIC COUNT" button 155. In this regard, it may be automatically judged whether the names of the medicines are coincident or not. Further, it may be discriminably displayed that the names of the medicines are coincident and that the names of the medicines are not coincident.

When the "MANUAL INPUT" button 154 is manipulated, the number of the sheets for the blister pack 4 to be supplied is inputted through a ten key 156. Then, the number of the sheets is displayed on the display panel 152. The user fills the cassette 100 with the blister pack 4 as many as the displayed number of the sheets. Also, a data related thereto to is transmitted to and stored in the server by manipulating a "TRANSMISSION" button 157. When the "AUTOMATIC COUNT" button 155 is manipulated, if the user fills the cassette 100 with the blister packs 4, then the number of the sheets in the cassette 100 is automatically counted through a length measurement sensor 158 provided in an upper portion of the slope surface 151 (in this case, a rear end wall of the cassette 100 needs an opening for detection of the rearmost blister pack 4 without obstruction caused by the constant force spring). Further, when supplying the blister packs 4 is finished, similar to the foregoing, the "TRANSMISSION" button 157 is manipulated and a data related thereto is transmitted to and stored in the server.

As described above, when replenishing the cassette 100 with the blister packs 4 by using the filling unit 150, such task can be performed simply and efficiently since the cassette 100 is placed on the slope surface 151. Further, the number of the sheets for the blister packs 4 to be supplied can be manually or automatically transmitted to and stored in the sensor, thereby allowing for accurate check for the number of the sheets for the blister packs 4 in the cassette 100.

Seventh Embodiment

Figure 19:
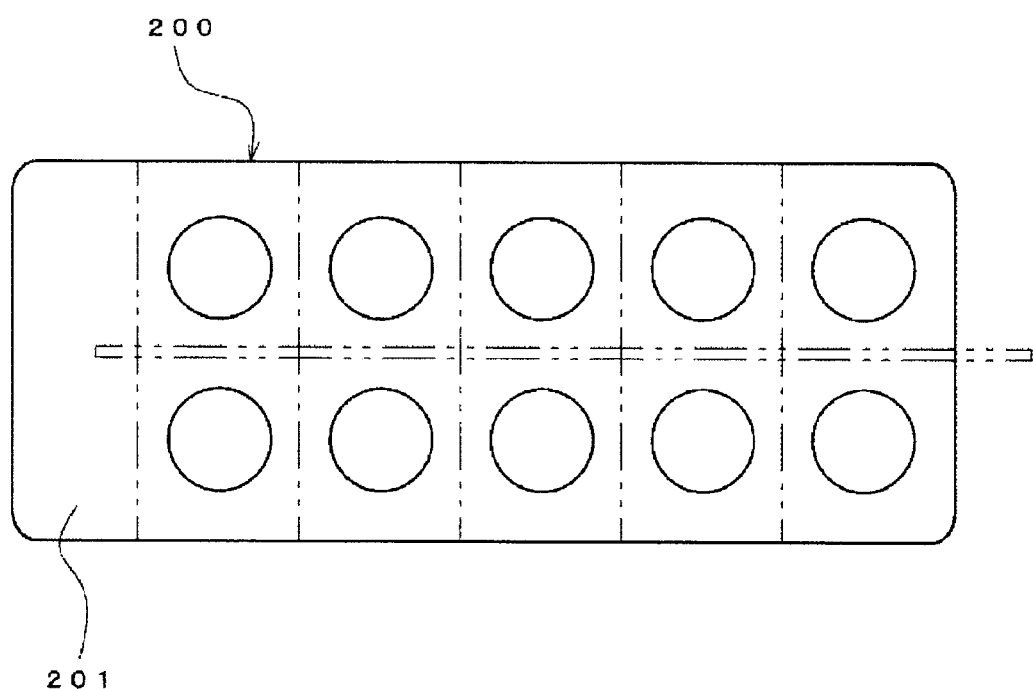
FIG. 19 is a front view of a blister pack in accordance with a seventh embodiment.

As shown in FIG. 19, a blister pack 200 having a gripping section 201 at its one end is used. In the blister pack, two rows run from the gripping section 201 and a plurality of medicines are packaged in each row one by one at a predetermined interval. In the blister pack 200, two medicines neighboring along each row make one pair. Also, a perforation line for cutting off is formed between the pairs (that is, in this embodiment, two tablets make a minimal unit that can be cut off by hands). When dispensing the fraction, the above-described cutting member 36 cut the blister pack along a two-dot chain line shown in FIG. 19.

Figure 20:
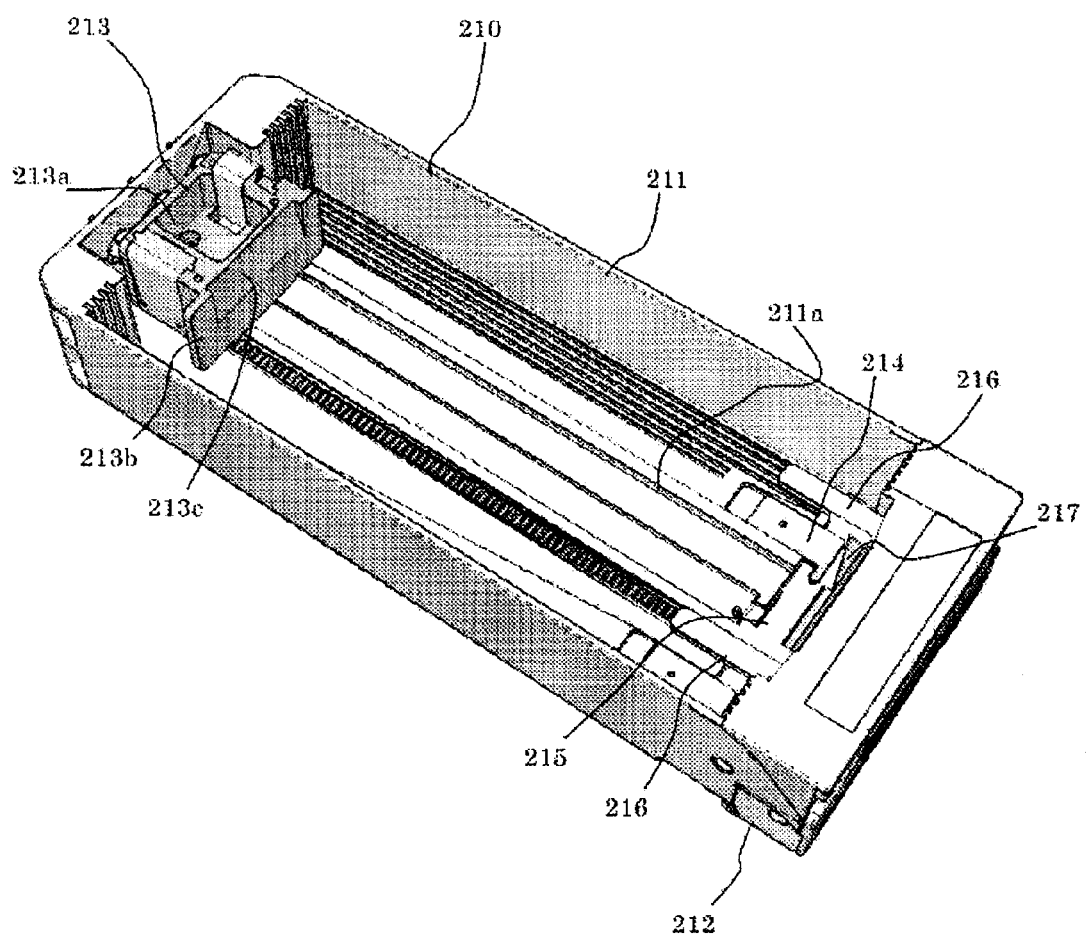
FIG. 20 is a perspective view of a cassette in accordance with the seventh embodiment.

The aforesaid blister pack 200 is contained in a cassette 210 constructed as shown in FIG. 20. The cassette 210 has nearly the same construction as the cassette 100 in the foregoing fourth embodiment. That is, the cassette includes a cassette body 211 and an opening/closing door 212 and further has the following features.

Specifically, an extruding member 213 with a constant force spring (CONSTON) is disposed in the cassette body 211. The extruding member has a generally rectangular parallelepiped shape. A hollow 213a with a thin thickness is formed on an upper surface and a protrusion (not shown) that slides in between two protrusion claws 211a formed on a bottom surface of the cassette body 211 is formed on a lower surface. A flange 213b projecting widthwise is formed in the front of the extruding member 213 and a recess 213c including a slope surface extending downwardly from the upper central surface is formed in the front of the extruding member. The recess 213c provides for a space for returning of the push-down portion 41 when the push-down portion 41 and the extruding member 213 interfere with each other during dispensing the final blister pack 200 remaining in the cassette body 211. Further, a recess 217 is formed on a front inner wall of the cassette body 211, thus avoiding or reducing the interference caused by slight shift in pushing-down position of the push-down portion 41.

Figure 24:
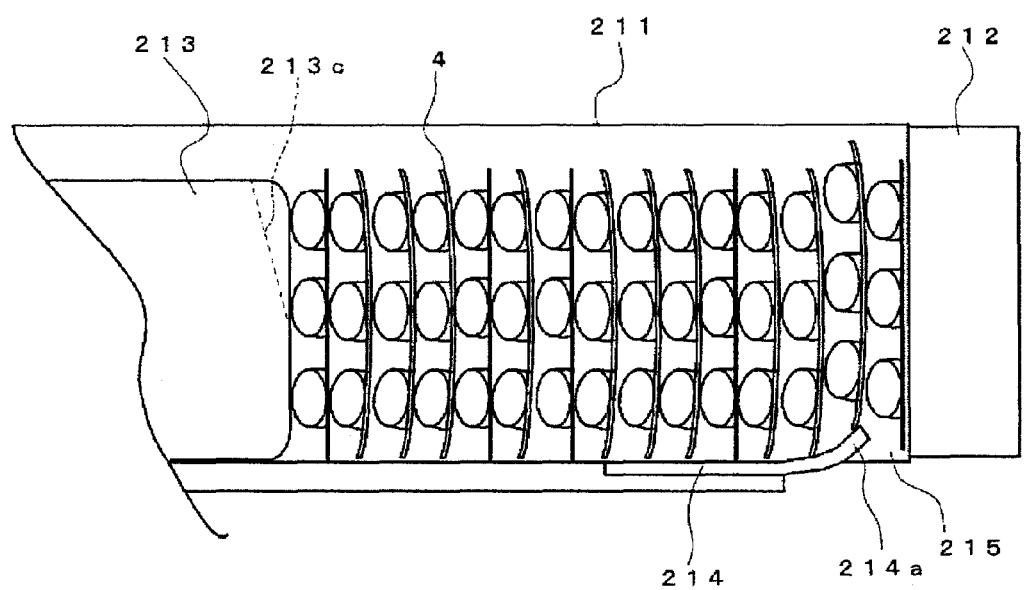
FIG. 24 is a schematic side view showing the cassette in accordance with the seventh embodiment.

Two sheets of guide plate 214 are attached to a bottom front end portion of the cassette body 211, instead of the pins located at two places, such that their position is adjustable forward and backward. Since the position of the guide plates 214 is adjusted, the blister pack 200 located next is prevented from moving together when the blister pack 200 is pushed down and passes through a communication opening 215. Preferably, a leading end portion of the guide plate 214 (e.g., a portion projecting toward the communication opening 215) includes a curved portion 214a curving upwardly. The curved portion 214a functions to raise the foremost blister pack 200 on the verge of being ejected from the cassette body 211 and to further put the same apart with respect to the next blister pack 200. In general, the blister packs 200 are supplied as accommodated in a box. Thus, as shown in FIG. 24, the blister pack has a shape wherein its projecting side with tablets contained therein is curved concavely. As such, only the foremost blister pack 200 may not be smoothly ejected from the communication opening 215 on occasion. However, as described above, the curved portion 214a is provided in the guide plate 214, thus placing the foremost blister pack 200 apart with respect to the next blister pack 200 and allowing only the foremost blister pack 200 to go over the curved portion 214a. This allows for reliable ejection.

Further, pressure pieces 216 that press against top edges of the blister packs 200 arranged one behind another are formed in the front inner wall of the cassette body 211 in two places along a width direction. The pressure pieces 216 are provided such that their positions are adjustable upwardly and downwardly according to the sizes of the blister packs 200. Further, when the foremost blister pack 200 has passed through the communication opening 215 and then the push-down portion 41 is lifted, the pressure pieces 216 prevent the next blister pack 200 contacting the push-down portion 41 and the further next blister pack 200 from rising up together.

When cutting off the fraction from the blister pack 200, each component is driven and controlled as follows (fraction cutting process).

Figure 21:
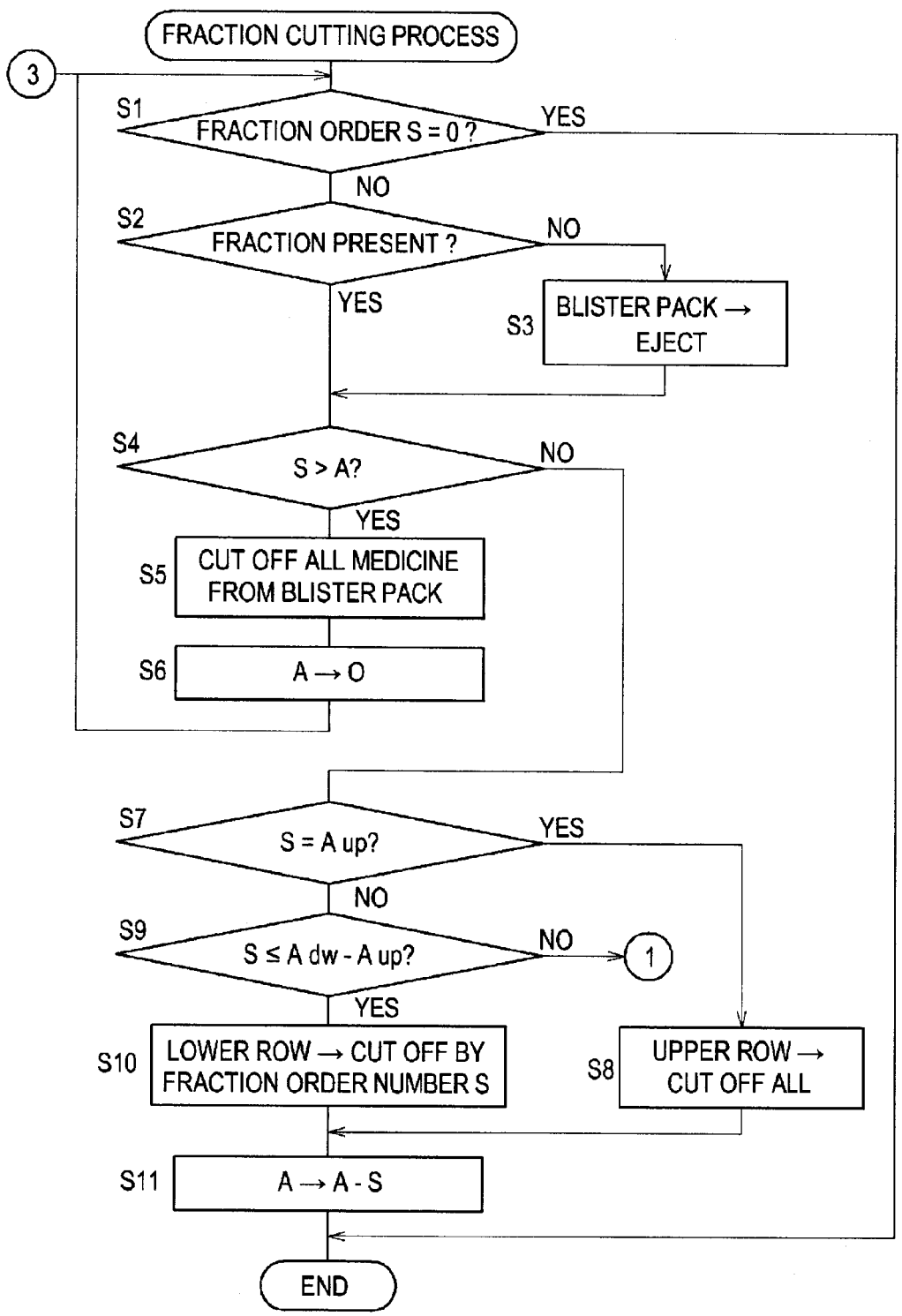
FIG. 21 is a flow chart showing a fraction cutting process in accordance with the seventh embodiment.
Figure 22:
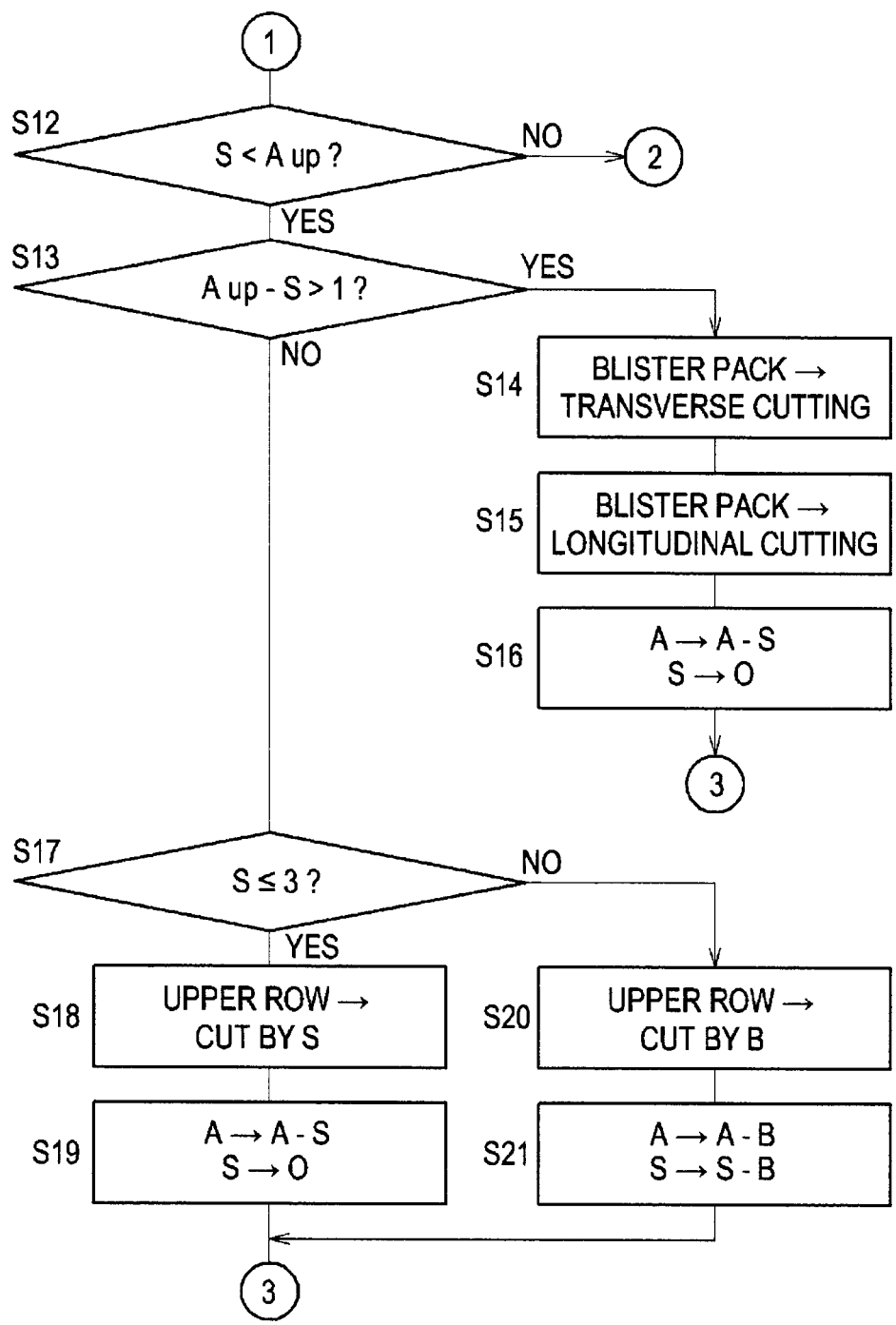
FIG. 22 is a flow chart showing a fraction cutting process in accordance with the seventh embodiment.
Figure 23:
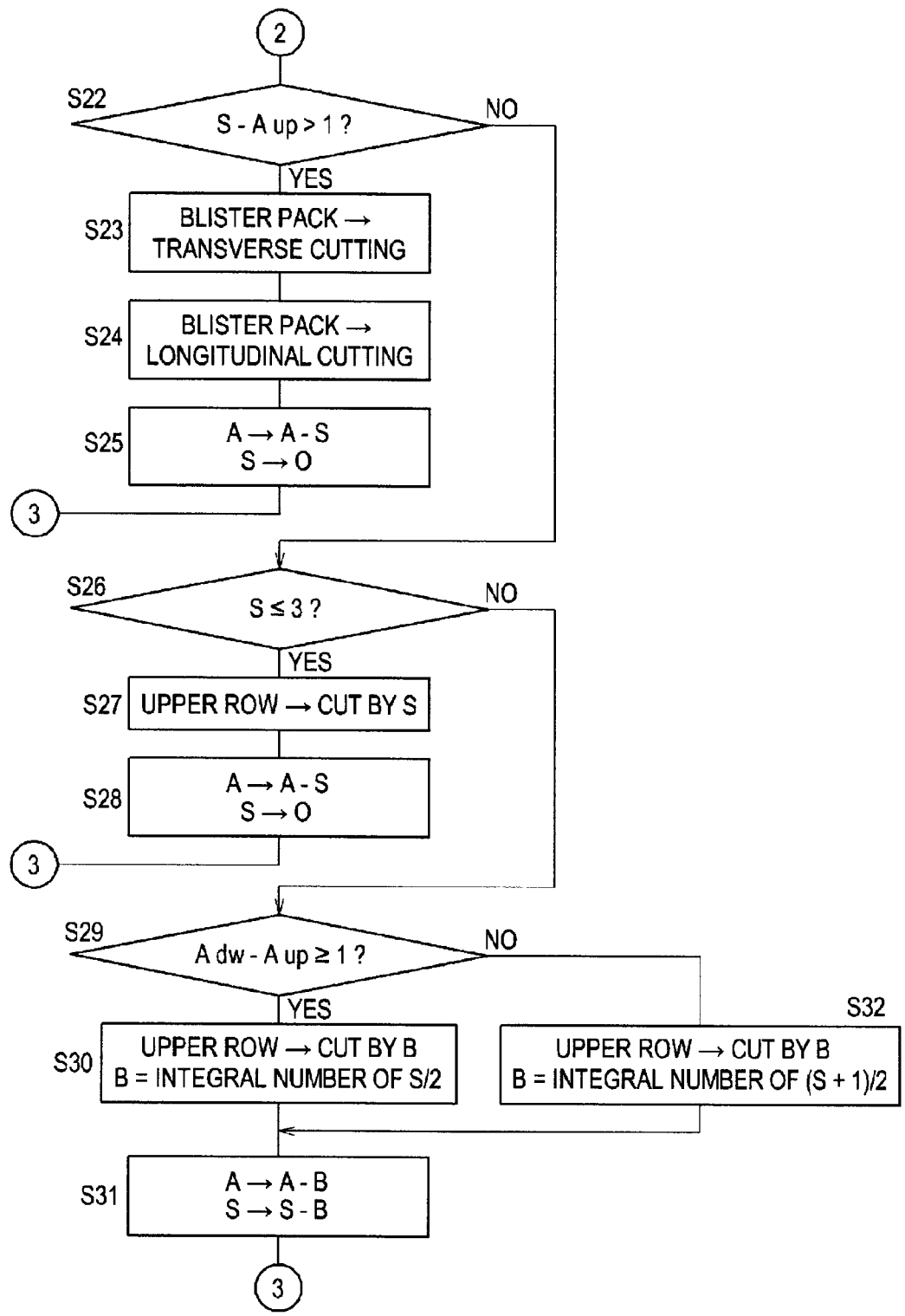
FIG. 23 is a flow chart showing a fraction cutting process in accordance with the seventh embodiment.

Specifically, as shown by the flow charts in FIGS. 21 to 23, it is first judged whether a fraction order is included in a transmitted or inputted medicine dispensing instruction (i.e., whether a data including the fraction is absent in the medicine dispensing instruction (S=0) or not) (Step S1). If the fraction order is present, it is judged whether the blister pack 200 to be fractionized (the remainder of the blister pack 200 after the fraction of medicines is cut off therefrom) is retained in the opening/closing door 212 (Step S2). If not retained, similar to the foregoing fourth embodiment, the opening/closing door 212 is opened and the blister pack 200 is ejected from the cassette 200 to the opening/closing door 212 (Step S3).

Subsequently, it is determined whether the fraction order number S is greater than a medicine stock number A (the number of the medicines in the blister pack 4 to be fractionized that is retained in the opening/closing door 212) (Step S4). If the fraction order number S is greater than the medicine stock number A, the blister pack 200 to be fractionized is cut by a predetermined dimension from its one end and is thus divided into upper and lower rows with the gripping section 201 remaining. Subsequently, the blister pack 200 to be fractionized is cut from the gripping section 201 and thereby all the medicines are cut off from the gripping section 201 (Step S5). That is, all the medicines within the blister pack 200 to be fractionized are dispensed. Thereafter, the medicine stock number A is updated and set to "0" (Step S6) and the fraction cutting process returns to the Step S1 and repeats the aforesaid steps.

If the fraction order number S is equal to or less than the medicine stock number A, then it is determined whether the fraction order number S is equal to the number of tablets Aup in the upper row of the blister pack 200 to be fractionized (Step S7). If the fraction order number S is equal to the number of tablets Aup in one of the rows of the blister pack 200 to be fractionized (in this case, the upper row), then all the medicines in the upper row of the blister pack 200 to be fractionized (Step S8) are cut. Thereafter, the medicine stock number A is updated to (A−S) (Step S11) and the fraction cutting process is finished. If the fraction order number S is not equal to the number of tablets Aup in the upper row of the blister pack 200, then it is determined whether the number of medicines (Adw−Aup) within a portion of the other row (in this case, the lower row) sticking out over the upper row is equal to or greater than the fraction order number S (Step S9).

If the number of medicines (Adw−Aup) is equal to or greater than the fraction order number S, then the lower row is cut by the fraction order number S (Step S10). Thereafter, similar to the foregoing, the medicine stock number A is updated to (A→A−S) (Step S11) and the fraction cutting process is finished.

If the number of medicines within the sticking-out portion is equal to less than the fraction order number S, then it is determined whether the number of medicines Aup in the upper row is greater than the fraction order number S (Step S12). If the number of medicines Aup in the upper row is greater than the fraction order number S, it is judged whether the number of medicines in the upper row remaining after cutting is equal to or greater than two (Aup−S>1) (Step S13). This is for preventing the number of remaining medicines from being one so that only one medicine cannot be dispensed in next cutting.

When the number of medicines Aup in the upper row remaining after cutting becomes two or more, the blister pack 200 is cut by a predetermined dimension from its one end (transverse cutting) and thereby is divided into two upper and lower rows (Step S14). Subsequently, the blister pack 200 is turned at 90 degrees and the upper row is cut by the fraction order number S (longitudinal cutting) (Step S15). And, the medicine stock number A is updated to (A→A−S) and the fraction order number S is updated to (S→0) (Step S16).

When the number of medicines Aup in the upper row remaining after cutting becomes one, it is judged whether the fraction order number 3 is equal to or less than three (Step S17). When the fraction order number S is equal to or less than three, the remainder of the upper row becomes four or less. Thus, it is judged the cutting cannot be performed in a desired cutting manner and the upper row is cut by the fraction order number S (Step S18). Subsequently, the medicine stock number A is updated to (A→A−S) and the fraction order number S is updated to (S→0) (Step S19). On the contrary, when the fraction order number S exceeds four, the medicines within the upper row are cut off by a value B obtained by adding one (1) to the fraction order number S and then dividing the same with two (2) (Step S20). Subsequently, the medicine stock number A is updated to (A→A−B) and the fraction order number S is updated to (S→S−B) (Step S21). Then, the fraction cutting process returns to the Step S1 and repeats the aforesaid steps.

If the number of medicines Aup in the upper row is equal to or less than fraction order number S (Step S12: NO), similar to the foregoing, then it is determined whether the number of medicines in the upper row remaining after next cutting is two or more (S−Aup>1?) (Step S22). If the number of medicines in the upper row remaining after cutting becomes two or more, the blister pack 200 is cut by a predetermined dimension from its one end (transverse cutting) and is thus divided into two upper and lower rows (Step S23). Subsequently, the blister pack 200 is turned at 90 degrees and the upper row is cut according to the fraction order number S (Step S24). And, the medicine stock number A is updated to (A→A−S) and the fraction order number S is updated to (S→0) (Step S25). Then, the fraction cutting process returns to the Step S1 and repeats the aforesaid steps.

If the number of medicines in the upper row remaining after cutting is one (Step S22: NO), it is judged whether the fraction order number S is three or less (Step S26). If the fraction order number S is three or less, the upper row is cut (Step S27). Also, the number A of the remaining medicines of the blister pack 200 is updated to (A→A−S) and the fraction order number S is updated to (S→0) (Step S28). If the fraction order number S exceeds three, it is judged whether the number of medicines in the lower row is greater than the number of medicines in the upper row (Step S29). If the number of medicines in the lower row is greater than the number of medicines in the upper row, the upper row is cut by a half of the faction order number S (Step S30). And, the number A of the remaining medicines of the blister pack 200 is updated to (A→A−B) and the fraction order number S is updated to (S→S−B) (Step S31). Further, if the number of medicines in the lower row is equal to or less than the number of medicines in the upper row, the medicines as many as an integral number of a value B obtained by adding one to the fraction order number S and then dividing the same with two are cut off from the upper row (Step S32) and then the fraction cutting process proceeds to the Step S31. Thereafter, the fraction cutting process returns to the Step S1 and repeats the aforesaid steps. As a result, where the fraction order number S becomes "0" (Step S1: YES), the aforesaid serial processes are finished.

As described above, the foregoing embodiment can cut the blister pack 200 according to the fraction order such that the cut medicine cannot be one at least. That is, if the cut medicine is one, then the patient can take the medicine by mistake without removing the same from the package. However, the foregoing embodiment can prevent such an accident previously. Further, as a cutting method for achieving that, the blister pack 200 is grasped by the medicine group of the upper and lower rows and is turned at 90 degrees. Thus, appropriate cutting can be performed with a single cutting member 36.

Further, according to the foregoing seventh embodiment, the blister pack 200 is cut first in a transverse orientation, that is with the medicine group arranged in two upper and lower rows. Then, the blister pack is cut in a longitudinal orientation. However, the orientation of the blister pack 200 in cutting may be freely changed according to the construction of the cutting member 36.

Further, in the foregoing seventh embodiment, the transverse cutting may be performed in a manner of completely bisecting the medicines in the upper and lower rows to leave the gripping section 201 or cutting off the medicines by a necessary number whenever necessary. Further, the blister pack may be bisected as leaving the final one medicine adjacent to the gripping section 201 (two medicines in the upper and lower rows). In such a case, only final two medicines in the upper and lower rows can be collectively cut off, thus reducing the frequency with which only one medicine is dispensed.

Moreover, the blister pack 200 with medicines packaged therein in two rows is illustrated with regard to the foregoing seventh embodiment. However, the blister pack may have three or more rows and show the same effect by cutting off its fraction as described above. Specifically, the processes posterior to the Step S7 in the flow chart shown in FIG. 21 may be added according to the number of the rows.

Additionally, according to the foregoing embodiments, only one blister pack 200 is permitted to pass by the following manner: closing a portion of the dispensing opening 15 of the cassette body 9, 101, 211 by means of the closure piece 16 biased by the spring 16 or by means of the fixed closure piece 16; or projecting the pin or the guide plate 214 to the portion of the dispensing opening 15. However, either the combination including the fixed closure plate 16 and the guide plate 214 having elasticity or the combination including the closure plate 16 biased by the spring 17 and the guide plate 214 having stiffness may be used.

Eighth Embodiment

Figure 25:
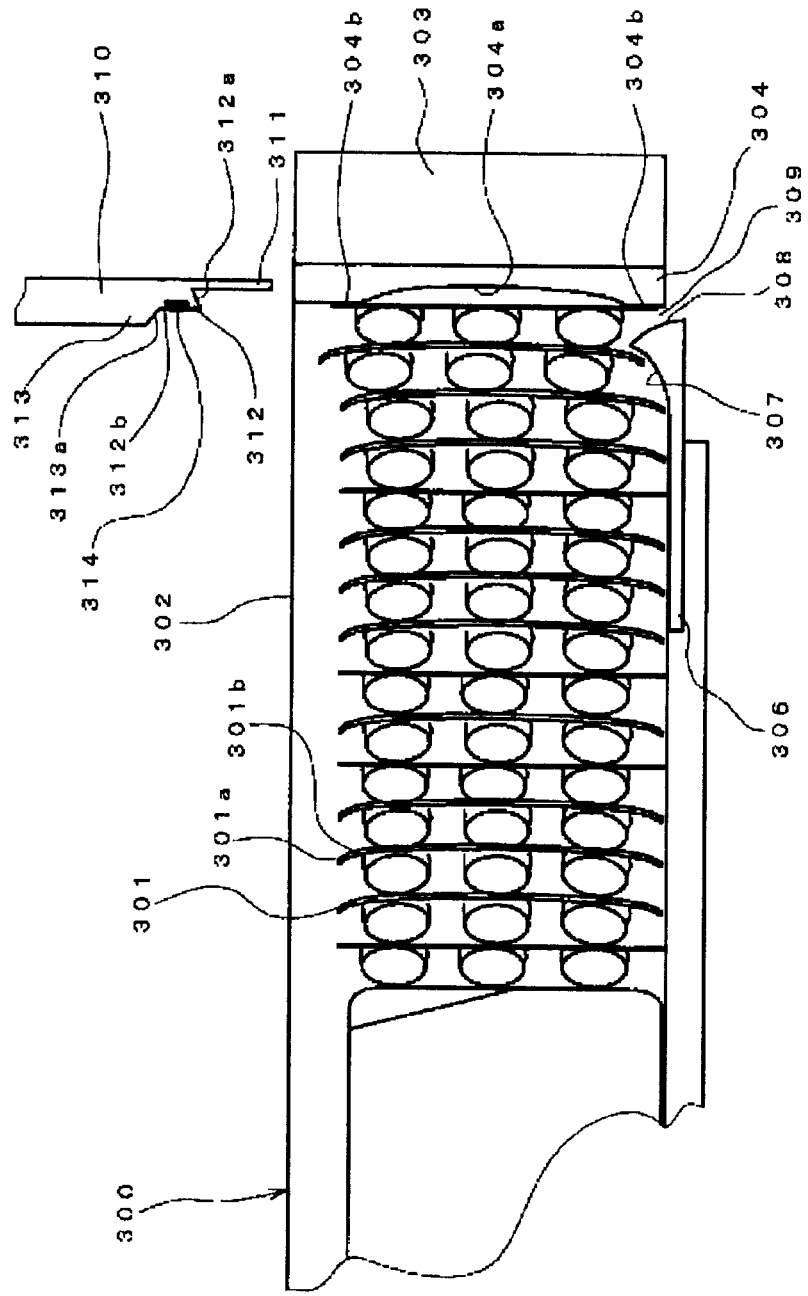
FIG. 25 is a side sectional view showing a portion of a cassette in accordance with an eighth embodiment.
Figure 26:
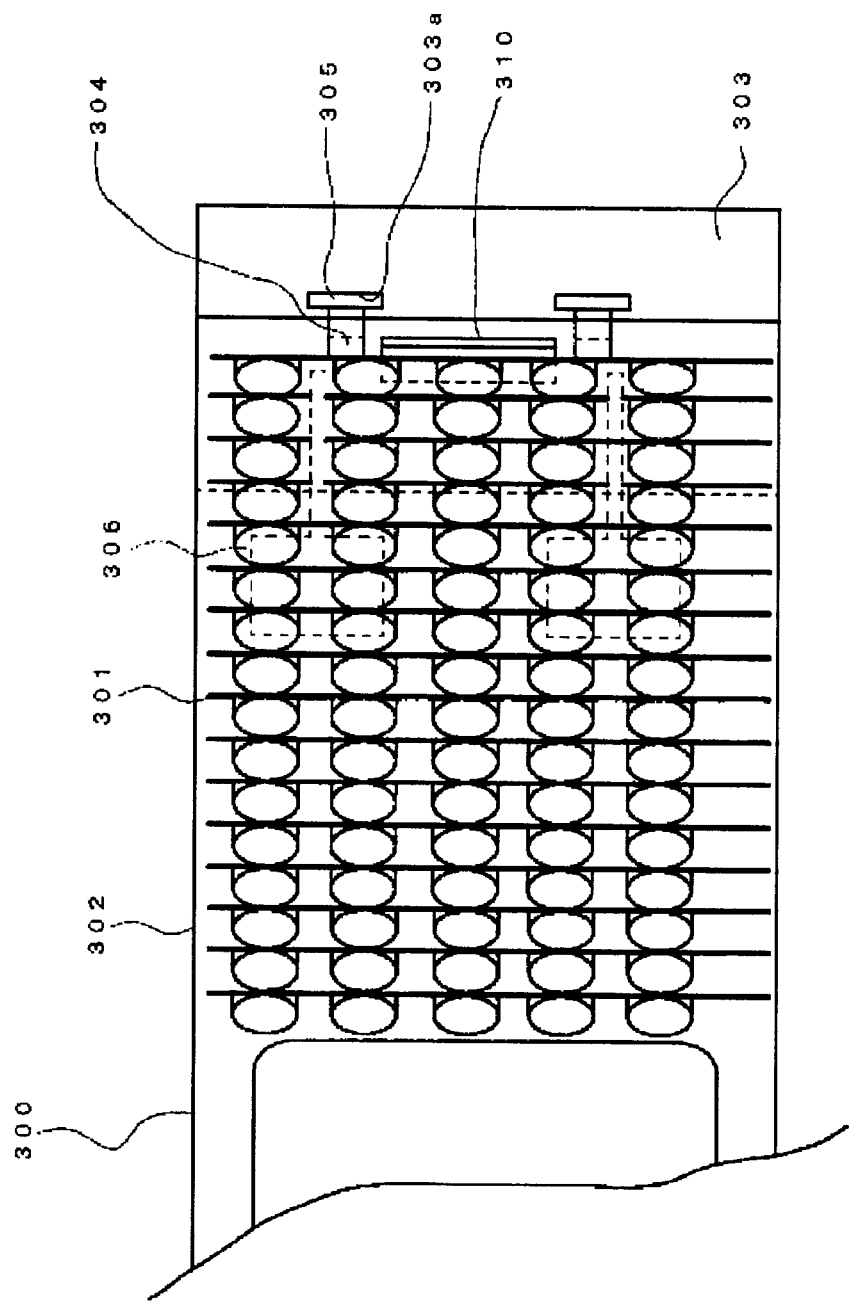
FIG. 26 is a bottom view of FIG. 25.

A cassette 300 shown in FIGS. 25 and 26 is constructed to push a sheet side of a blister pack 301 (a side opposite to a swelled side with tablets therein) toward an end plate. As shown in FIG. 25, the blister pack 301 is apt to curve in its short direction. Thus, when an inner surface of the cassette 300 is formed flat and the blister pack 301 abuts the inner surface, the both edges of the blister pack can project inward and thus the blister pack cannot be ejected well from a dispensing opening 309. For such a reason, the eighth embodiment includes the construction described below.

Specifically, curvature receptors 304 are mounted at a predetermined interval in a width direction in two places of an inner surface of the end plate 303 that is located at one end of the cassette body 302, respectively. An external configuration of the curvature receptor 304 comprises an attaching portion 305 of generally T-shaped cross section as a whole. The attaching portion 305 is removably mounted to an attaching groove 303a formed on the end plate 303. The curvature receptor 304 has a curved surface 304a on its inner surface facing toward the inside of the cassette body 302. The curved surface 304a is formed to be most concave at an approximate central portion in a vertical direction (preferably, the central portion corresponds to a widthwise central portion of the blister pack 301 to be contained). Accordingly, the inner surface of the curvature receptor 304 has a shape gradually concave from upper and lower flat surfaces 304b toward the approximate center portion. Further, the maximum concave dimension of the curved surface 304a is set to be equal to or less than a thickness of the blister pack 301. Further, the curvature receptor 304 is detachable to the end plate 303 and is thus suitably replaceable according to different width dimensions and shapes of a sheet portion 301a of the blister pack 301.

Further, guide plates 306 are provided in a bottom front end of the cassette body 302 in two places in a width direction, respectively. Similar to the foregoing seventh embodiment, the guide plate 306 includes a first curved surface 307 that projects gradually upwardly toward the end plate 303. Further, a second curved surface (guide surface) 308 having a convex shape is provided from the first curved portion 307 to a leading end. The second curved surface 308 guides the blister pack 301 in contact therewith to the dispensing opening 309 and exerts a force in a direction of straightening the blister pack 301 when the blister pack curves in the short direction. The guide plate 306 is positionally adjustable in a width direction (a vertical direction in FIG. 26). Thus, the guide plate 306 can be positioned between the tablets of the blister pack 301. Further, the guide plate 306 is attached with a slight gap, which permits only one sheet portion 301a to pass therethrough, relative to the end plate 303. Thus, it is possible to firmly support the lower edge of the blister pack 301 located near the dispensing opening 309 and to prevent the blister packs from jamming or being dispensed as overlapped. Furthermore, the closure piece 16 described in the foregoing embodiments become unnecessary.

Further, a push-down portion 310 for ejecting the blister pack 301 from the cassette body 302 includes a guide portion 311 at a lower end of its plate-shaped body. A first receptor 312 is formed in an upper portion connected to the guide portion 311. The first receptor 312 includes a first receptor surface 312a projecting at an acute angle from the guide portion 311. The first receptor surface 312a can push down the edge of the sheet portion 301 of the blister pack 301. Further, a second receptor 313 is formed in an upper portion connected to the first receptor 312. The second receptor 313 includes a second receptor surface 313 projecting at an obtuse angle from the flat surface 312b extending from the first receptor 312. The second receptor surface 313a is brought into contact with a sheet surface 301b of the blister pack 301 that is curved enough to be not pushed down by the first receptor 312. Further, a frictional portion 314 is provided in the flat surface 312b extending from the first receptor 312. The frictional portion 314 is formed by adhering a material having high friction coefficient such as chloroprene rubber, neoprene rubber, etc. The curved blister pack 301 can be pushed down with the action of the second receptor surface 313a and the frictional portion 314. Also, the push-down portion 310 is constructed to be lowered down up to a position where the second receptor 313 passes by the guide plate 306 and can eject the blister pack 301 having great curvature.

Dispensing the blister pack 301 from the cassette 300 in the above-described eighth embodiment is as follows.

Specifically, the blister pack 301 in the cassette 300 is moved gradually upwardly by the first curved surface 307 of the guide plate 306a as going toward the one end. If the blister pack 301 reaches the second curved surface 308, then it is moved above the dispensing opening 309 (dispensing position) with a force of straightening a curved portion acting thereon.

In the dispensing position, the blister pack 301 is placed with the sheet surface 310b in abutment with the curvature receptor 304. That is, if the blister pack 301 is even, then its upper and lower edges are in abutment with the flat surfaces 304b of the curvature receptor 304. Further, where the blister pack 301 is curved in the short direction, the curved surface 304a of the curvature receptor 304 changes the abutment position of the sheet surface 301b. That is, the abutment position is not a central portion of the curved sheet surface 301b projecting at maximum, but other portion upwardly or downwardly apart from the central portion. Then, the curved and projecting portion is positioned to a concave portion formed by the curved surface 304a. Accordingly, a projection dimension of the upper and lower edges of the blister pack 301 (a projection dimension from the curvature receptor 304) can decrease.

If the push-down portion 310 is lowered down from such a state, then the guide portion 311 enters the gap formed between the end plate 303 and the foremost blister pack 301 by the curvature receptors 304.

When the blister pack 301 does not curve or it curves with a little curvature, the first receptor surface 312a of the first receptor is brought into abutment with a side edge of the sheet portion 31a of the blister pack 301. The first receptor surface 312a is formed at an acute angle. Thus, when the blister pack 301 is slightly curved, the first receptor surface guides the upper side edge in abutment therewith to the guide portion 311. Further, the second curved surface 308 of the guide plate 306 exerts a force to the lower side edge of the blister pack 301 toward the dispensing opening 309. Thus, the blister pack 301 is smoothly ejected from the dispensing opening 309.

Further, when the blister pack 301 is curved with a large curvature and the curved surface 304a of the curvature receptor 304 cannot absorb such a projection extent of the side edge, the second receptor surface 313a of the second receptor 313 and the frictional portion 314 in the push-down portion 310 are brought into abutment with the upper portion of the sheet surface 301b of the blister pack 301. Similar to the foregoing, the second curved surface 308 of the guide plate 306 exerts a force to the lower side edge of the blister pack 301 being in abutment therewith. Thus, the blister pack 301 can be ejected to the dispensing opening 309 although curved with a large curvature.

Further, to prevent a sheet of the blister pack 301 from falling down from the dispensing opening 309 when filling the cassette 300 with blister packs, a pivotal shutter for closing the dispensing opening 309 may be provided at the leading end of the second curved surface 308.

Further, according to the foregoing eighth embodiment, the first curved surface 307 and the second curved surface 308 are provided in the guide plate 306 as a guide surface. However, the guide surface is not limited to these curved surfaces, but may include other guide surface such as a slope surface.

The invention claimed is:

1. A medicine dispensing device, comprising:
   a device body;
   a container containing a plurality of blister packs with medicines packaged individually therein as the blister packs are arranged one behind another, the container being attached to the device body such that the blister packs are horizontally or substantially horizontally arranged one behind another;
   a dispensing member movably provided in the device body, the dispensing member being moved up to the container to dispense the blister pack contained in the container;
   a gripping member gripping and carrying the blister pack dispensed by the dispensing member; and
   a cutting member cutting off a fraction from the blister pack gripped and carried by the gripping member,
   wherein the container includes:
   a dispensing opening formed in a bottom of the container at one end of the container for dispensing the blister pack;
   a biasing means for biasing the contained blister packs toward the one end; and
   an opening/closing door pivotally disposed at one end surface,
   wherein the opening/closing door includes a retaining portion retaining the blister pack ejected from the dispensing opening of the container,
   wherein the opening/closing door is positionable to an opened position for retaining the blister pack, which is dispensed from the dispensing opening by the dispensing member, to the retaining portion, and
   wherein the gripping member is configured to grip the blister pack retained by the retaining portion in the opened position and to carry the blister pack to the cutting member and is configured to carry the remainder of the blister pack with the fraction cut off for retention in the retaining portion.

2. The medicine dispensing device of claim 1, further comprising a position adjusting member adjusting a relative position between the blister pack gripped by the gripping member and the cutting member to change a cutting position for the blister pack.

3. The medicine dispensing device of claim 1, wherein the container is configured to open the opening/closing door when the container is drawn out from the device body and is positioned to a medicine dispensing position.

4. The medicine dispensing device of claim 1, wherein the blister pack contains a plurality of medicines in two rows,
   wherein the medicine dispensing device further comprises a control means, the control means allowing the cutting means to first cut one of the rows in a range that a remainder number after cutting does not become one and further to cut the other of the rows when the blister pack is cut by the cutting member based on a fraction order included in a medicine dispensing instruction.

5. The medicine dispensing device of claim 4, wherein the control means allows the other of the rows to be cut first when the remainder number of the one of the rows is less than a remainder number of the other of the rows and the remainder number of the other of the rows is equal to or less than a fraction order number.

6. The medicine dispensing device of claim 4, wherein when a fraction order number indicated in the fraction order is greater than the remainder number of the one of the rows of the blister pack, the control means divides the fraction order number and allows the one of the rows to be cut by an obtained division number and thereafter allows the other of the rows to be cut.

7. The medicine dispensing device of claim 1, wherein a guide plate is disposed on the bottom of the container along a biased direction of the contained blister packs,
   wherein the guide plate includes a first guide surface gradually higher toward the dispensing opening and a second guide surface connected to the first guide surface and being gradually lower toward the dispensing opening.

8. The medicine dispensing device of claim 1, wherein the container includes a curvature receptor projecting inwardly from an inner end surface located at the dispensing opening, the curvature receptor including a flat surface configured to abut a sheet surface of a blister pack and a curved surface forming a relief for a swelled portion of a curved blister pack.

* * * * *